US012576116B2

(12) United States Patent
Navarro López et al.

(10) Patent No.: US 12,576,116 B2
(45) Date of Patent: Mar. 17, 2026

(54) USE OF PROBIOTICS IN THE TREATMENT AND/OR PREVENTION OF ATOPIC DERMATITIS

(71) Applicants: BIONOU RESEARCH, S.L., Sant Joan d'Alacant (ES); BIOPOLIS, S.L., Paterna (ES)

(72) Inventors: Vicente Manuel Navarro López, Onil (ES); Ana Adela Ramírez Boscá, Alicante (ES); José Manuel Pérez Orquín, Alcoy (ES); Daniel Ramón Vidal, La Eliana (ES); Salvador Genovés Marténez, Aldaia (ES); María Empar Chenoll Cuadros, La Pobla de Vallbona (ES); Francisco Manuel Codoñer Cortés, Catarroja (ES)

(73) Assignees: BIONOU RESEARCH, S.L., Sant Joan d'Alacant (ES); BIOPOLIS, S.L., Paterna (ES)

( * ) Notice: Subject to any disclaimer, the term of this patent is extended or adjusted under 35 U.S.C. 154(b) by 0 days.

(21) Appl. No.: 16/318,684

(22) PCT Filed: Jul. 18, 2017

(86) PCT No.: PCT/EP2017/068131
§ 371 (c)(1),
(2) Date: Jan. 17, 2019

(87) PCT Pub. No.: WO2018/015388
PCT Pub. Date: Jan. 25, 2018

(65) Prior Publication Data
US 2019/0282636 A1 Sep. 19, 2019

(30) Foreign Application Priority Data

Jul. 18, 2016 (EP) .................................... 16382342

(51) Int. Cl.
| | |
|---|---|
| A61K 35/745 | (2015.01) |
| A23L 33/135 | (2016.01) |
| A61K 9/00 | (2006.01) |
| A61K 35/747 | (2015.01) |
| A61P 17/00 | (2006.01) |

(52) U.S. Cl.
CPC .......... *A61K 35/745* (2013.01); *A23L 33/135* (2016.08); *A61K 9/0019* (2013.01); *A61K 35/747* (2013.01); *A61P 17/00* (2018.01)

(58) Field of Classification Search
None
See application file for complete search history.

(56) References Cited

U.S. PATENT DOCUMENTS

| | | | | |
|---|---|---|---|---|
| 2006/0171936 A1* | 8/2006 | Gueniche | ................ | A61P 17/16 |
| | | | | 424/93.45 |
| 2013/0224166 A1* | 8/2013 | Mercenier | ............... | A23P 10/40 |
| | | | | 424/93.44 |
| 2014/0348796 A1* | 11/2014 | Burcelin | .............. | A61K 31/155 |
| | | | | 424/93.3 |
| 2014/0369965 A1 | 12/2014 | Herranz et al. | | |
| 2016/0143963 A1 | 5/2016 | Martorell | | |

FOREIGN PATENT DOCUMENTS

| | | | | |
|---|---|---|---|---|
| CN | 101165162 A | 4/2008 | | |
| CN | 103619343 A | 3/2014 | | |
| CN | 103705543 A | 4/2014 | | |
| CN | 104605277 A | 5/2015 | | |
| EP | 2228067 A | 9/2010 | | |
| EP | 2236598 A1 | 10/2010 | | |
| JP | 2004250337 A | 9/2004 | | |
| KR | 20130049554 A | 5/2013 | | |
| KR | 20150068670 A | 6/2015 | | |
| KR | 20160053447 A | 5/2016 | | |
| WO | WO2015007941 A1 * | 1/2015 | ............... | C12N 1/20 |

OTHER PUBLICATIONS

Karimi et al. (The anti-obesity effects of Lactobacillus casei strain Shirota versus Orlistat on high fat diet-induced obese rats. Food & Nutrition Research 2015, 59: 29273).*
Dao et al. (Losing weight for a better health: Role for the gut Microbiota. Clinical Nutrition Experimental 6 (Apr. 2016) 39e58).*
Olivares et al. (Double-blind, randomised, placebo-controlled intervention trial to evaluate the effects of Bifidobacterium longum CECT 7347 in children with newly diagnosed coeliac disease. British Journal of Nutrition (2014), 112, 30-40).*
Venkatasubramani et al. (Obesity in Pediatric Celiac Disease. JPGN vol. 51, No. 3, Sep. 2010 pp. 295-297).*
Moal et al. (Anti-Infective Activities of Lactobacillus Strains in the Human Intestinal Microbiota: from Probiotics to Gastrointestinal Anti-Infectious Biotherapeutic Agents. 2014. Clinical Microbiology Reviews: 27(2)p. 167-199.*
Prozema et al. (pp. 1-4, copyright 2021).*
Martin et al. Review of Infant Feeding: Key Features of Breast Milk and Infant Formula. Nutrients 2016, 8, 279; pp. 1-11.*
Hanifin et al. "Diagnostic Features of Atopic Dermatitis", Acta Dermato Venereologica, 1980; vol. 92, pp. 44-47.

(Continued)

*Primary Examiner* — Sharmila G Landau
*Assistant Examiner* — Natalie M Moss
(74) *Attorney, Agent, or Firm* — Hayes Soloway PC

(57) ABSTRACT

The present invention is intended for the use of a probiotic composition comprising *Bifidobacterium animalis* subs. *lactis* (*B. lactis*), *Bifidobacterium longum* and *Lactobacillus casei*, particularly the strains *B. lactis* CECT 8145, *B. longum* CECT 7347 and/or *L. casei* CECT 9104, in the treatment and/or prevention of atopic dermatitis.

1 Claim, 11 Drawing Sheets

(56) References Cited

OTHER PUBLICATIONS

Kunz et al., "Clinical Validation and Guidelines for the SCORAD Index: Consensus Report of the European Task Force on Atopic Dermatitis", Nov. 28, 1996, Dermatology, vol. 195, pp. 10-19.

F. Muñoz López, "Dermatitis atópica en la edad infantil. Valoración de la gravedad y tratamiento", 2002, JANO, 1432: pp. 52-57.

Boguniewitcz et al., "Atopic dermatitis", Jul. 2006, Journal of Allergy and Clinical Immunology, vol. 118, No. 1, pp. 40-43.

Leung et al., "Atopic dermatitis", Jan. 11, 2003, The Lancet, vol. 361, pp. 151-160.

Kim et al., "Effects of probiotics for the treatment of atopic dermatitis: a meta-analysis of randomized controlled trials", Aug. 2014, Annals of Allergy, Asthma and Immunology, vol. 113, No. 2, pp. 217-226.

Gerasimov et al., "Probiotic Supplement Reduces Atopic Dermatitis in Preschool Children: A Randomized, Double-Blind, Placebo-Controlled, Clinical Trial", 2010, American Journal of Clinical Dermatology, vol. 11, No. 5, pp. 351-361.

Farid et al., "Effect of a New Synbiotic Mixture on Atopic Dermatitis in Children: a Randomized-Controlled Trial", Jun. 2011, Iranian Journal of Pediatrics. vol. 21, No. 2, pp. 225-230.

Van der Aa et al., "Effect of a new synbiotic mixture on atopic dermatitis in infants: a randomized-controlled trial", Nov. 26, 2009, Clinical and Experimental Allergy, vol. 40, No. 5, pp. 795-804.

Boyle et al., "Probiotics for treating eczema (Review)", 2008, The Cochrane Review, Issue 4: CD006135.

Lee et al., "Meta-analysis of clinical trials of probiotics for prevention and treatment of pediatric atopic dermatitis", Jan. 2008, Journal of Allergy and Clinical Immunology, vol. 121, No. 1, pp. 116-121.

Klindworth et al., "Evaluation of general 16S ribosomal RNA gene PCR primers for classical and next-generation sequencing-based diversity studies", Aug. 28, 2012, Nucleic Acids Research, vol. 41, No. 1.

Zhang et al., "PEAR: a fast and accurate Illumina Paired-End reAd merger", Mar. 1, 2014. Bioinformatics, vol. 30, No. 5, pp. 614-620.

Marcel Martin, "Cutadapt removes adapter sequences from high-throughput sequencing reads", May 2011, EMBnet.journal, vol. 17, No. 1, pp. 10-12; Available at: <http://journal.embnet.org/index.php/embnetjournal/article/view/200>.

Edgar et al., "UCHIME improves sensitivity and speed of chimera detection", Jun. 23, 2011, Bioinformatics vol. 27, No. 16, pp. 2194-2200.

Altschul et al., "Basic Local Alignment Search Tool", May 15, 1990, Journal of Molecular Biology, vol. 215, No. 3, pp. 403-410.

Arumugam et al., "Enterotypes of the human gut microbiome", May 12, 2011, Nature, vol. 473, No. 7346, pp. 174-180.

Dave et al. "The human gut microbiome: current knowledge, challenges, and future directions", May 8, 2012, Translational Research, vol. 160, No. 4, pp. 246-257.

Database WPI Week 201645 Thomson Scientific, London, GB; AN 2016-30967X XP002764923, May 13, 2016.

Database WPI Week 201340 Thomson Scientific, London, GB; AN 2013-H88136 XP002764924, May 14, 2013.

Database WPI Week 200461 Thomson Scientific, London, GB; AN 2004-630667 XP002764925, Sep. 9, 2004.

Seo et al., "Alleviation of Atopic Dermatitis through Probiotic and Mixed-probiotic Treatments in an Atopic Dermatitis Model", Han-Gug Chugsan Sigpum Hag-Hoeji—Korean Society for Food Science of Animal Resources, vol. 31, No. 3, Jun. 30, 2011, pp. 420-427.

Akay et al., "The relationship between bifidobacteria and allergic asthma and/or allergic dermatitis: A prospective study of 0-3 years-old children in Turkey'", Anaerobe, vol. 28, Aug. 1, 2014, pp. 98-103.

Extended European Search office search report, dated Jan. 10, 2017, for EP Application No. 16382342.0-1466.

International Search Report and Written Opinion of the International Searching Authority, dated Jul. 18, 2017, for PCT Application No. PCT/EP2017/068131.

Hanifin et al., "Diagnostic Features of Atopic Dermatitis", Acta Dermatovener (Stockholm) Supplement, vol. 60, No. 92, Jan. 1980, pp. 44-47.

Kunz et al., "Clinical Validation and Guidelines for the SCORAD Index: Consensus Report of the European Task Force on Atopic Dermatits", Dermatology vol. 195, Nov. 28, 1996, pp. 10-19.

Marcel Martin, "Cutadapt removes adapter sequences from high-throughput sequencing reads", EMBnet Journal, vol. 17, No. 1, May 2, 2011.

F. Muñoz López, "Dermatitis atópica en la edad infantil. Valoración de la gravedad y tratamiento", Diagnóstico, Aug. 12, 2006.

F. Muñoz López, "Dermatitis atópica en la edad infantil. Valoración de la gravedad y tratamiento", Diagnóstico, Jan. 2002—with English Translation enclosed.

Notice of Reasons for Refusal of the Japanese Patent Office dated Apr. 27, 2021 for related Japanese Patent Application No. 2019-503412.

Amazon site, [online], 2015, [search on (Apr. 15, 2021)] Internet <URL:https://www.amazon.com/Physique-Formula-Ultra-Probiotic-Bifdobacterium/dp/B018J8JB4A>.

Amazon site, [online], 2016.5, [search on (Apr. 15, 2021)], Internet <URL:https://www.amazon.com/Dr-Mercola-Complete-Probiotics-Supplement/dp/B073Q4YBXZ>.

Guerrero-Garcia et al., "Combination therapy in the treatment of hypertension" Drugs in Context, vol. 7:212531, Jun. 6, 2018, pp. 1-9.

Frishman et al., "A multifactorial trial design to assess combination therapy in hypertension" Archives of Internal Medicine, Jul. 11, 1994, vol. 154 No. 13, pp. 1461-1468.

De Milliano et al., "Is a multispecies pro biotic mixture effective in constipation during pregnancy? 'A pilot study," Article, 2012, vol. 11, No. 80, 6 pages, Nutrition Journal.

Cai et al., "Bifidobacterium lactic Meile et al. 1997 is a Subjective Synonym of Bifidobacterium animalis (Mitsuoka 1969) Scardovi and Trovatelli 1974," Article, 2000, vol. 44, No. 10, pp. 815-820, Microbiol. Immunol.

He et al., "Integrated Role of *Bifidobacterium animalis* subsp. lactis Supplementation in Gut Microbiota, Immunity, and Metabolism of Infant Rhesus Monkeys," Article, 2016, vol. 1, Issue 6, e000128-16, 15 pages, mSystems.

Rautava et al., "Maternal probiotic supplementation during pregnancy and breast-feeding reduces the risk of eczema in the infant," Article, Dec. 2012, pp. 1355-1360, J Allergy Clin Immunol.

\* cited by examiner

A
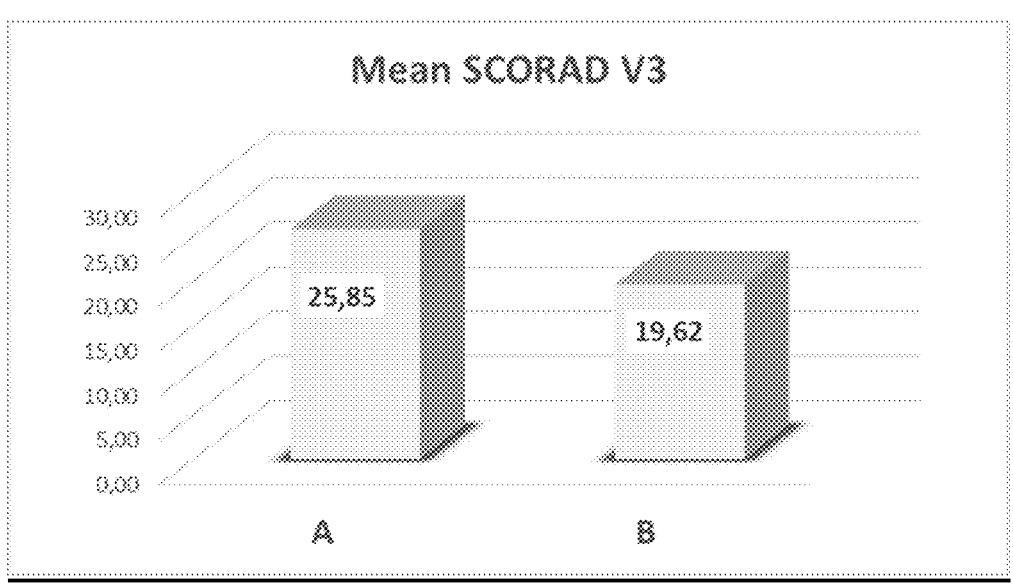
B
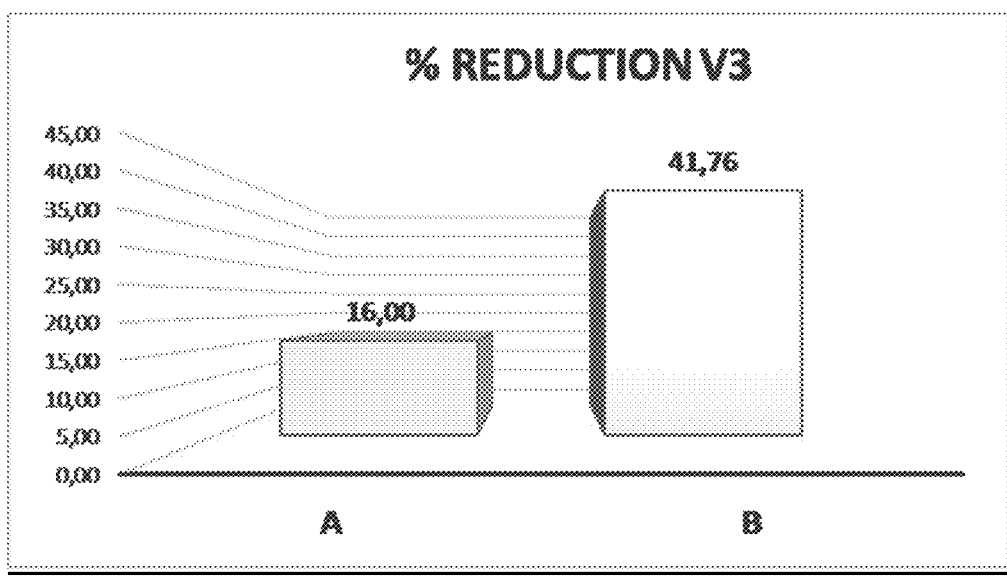
FIG. 6

A
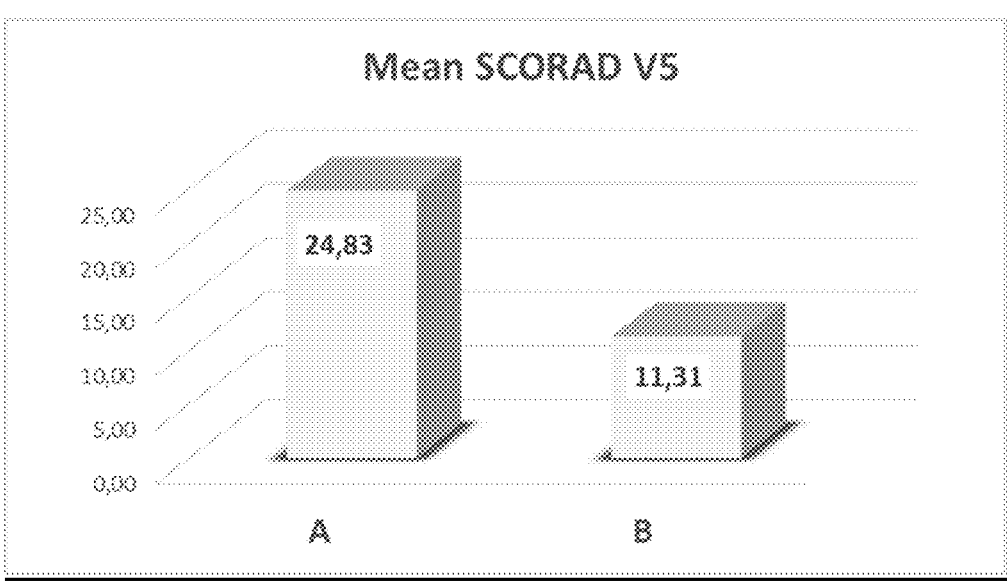
B
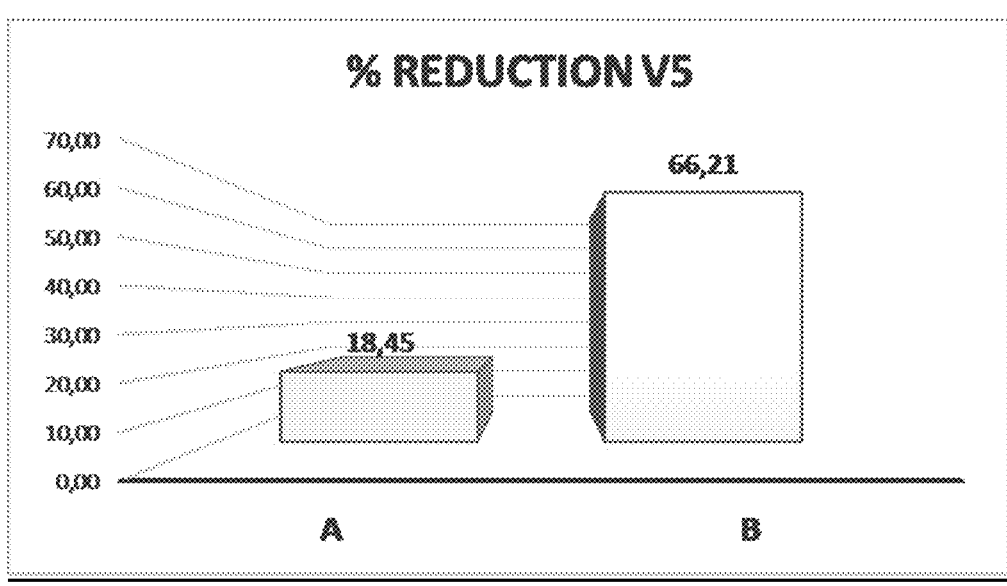
FIG. 7

<u>A</u>
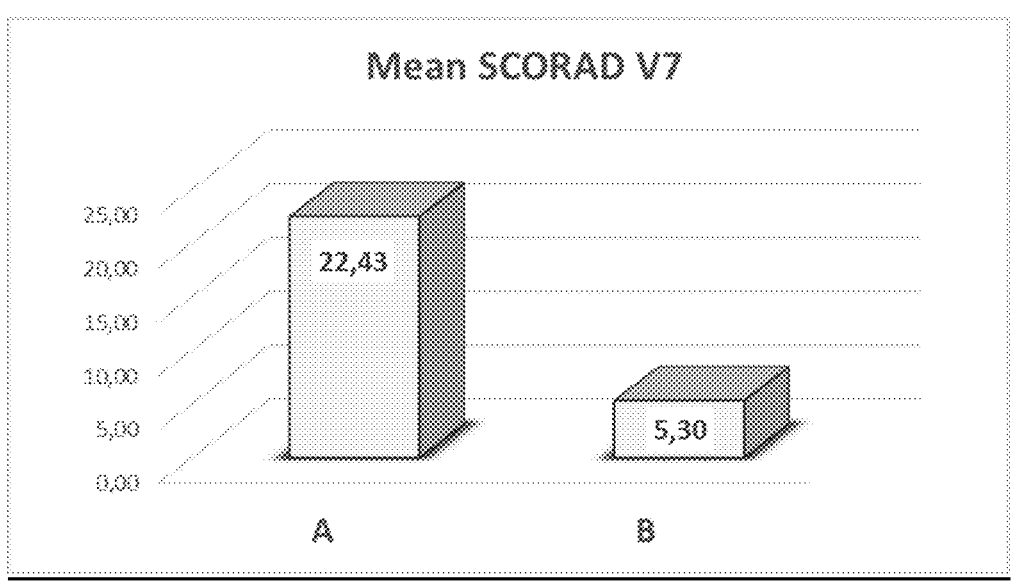
<u>B</u>
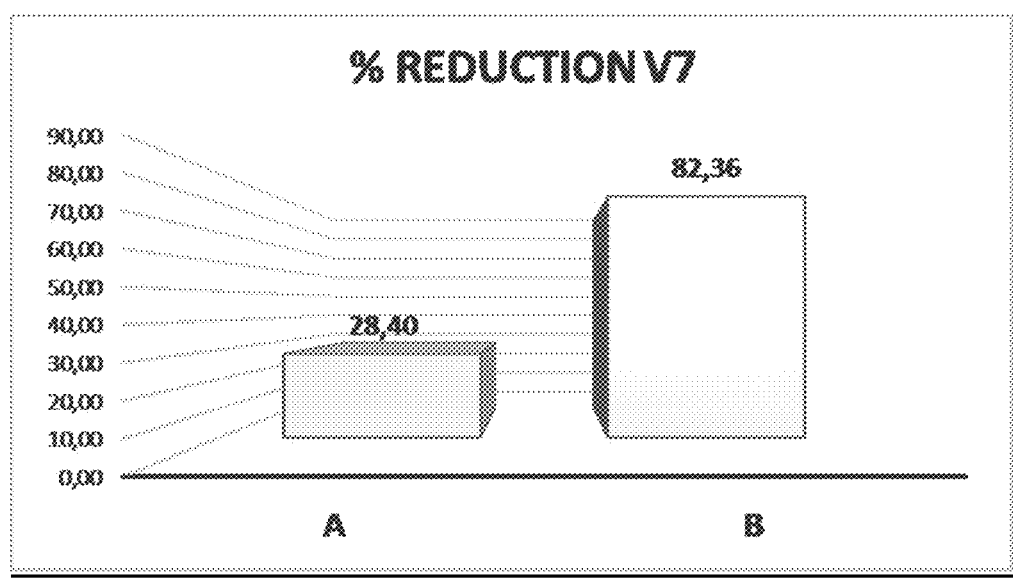
<u>FIG. 8</u>

SCORAD REDUCTION %

SCORAD EVOLUTION

USE OF PROBIOTICS IN THE TREATMENT AND/OR PREVENTION OF ATOPIC DERMATITIS

CROSS-REFERENCE TO RELATED APPLICATIONS

The present patent application is a national phase application of International Application No. PCT/EP2017/068131, filed Jul. 18, 2017, which claims priority to European Patent Application No. 16382342.0, filed Jul. 18, 2016, the disclosures of which are incorporated herein by reference.

The present invention relates to a probiotic composition and the use of said composition for the treatment and/or prevention of atopic dermatitis. Therefore, the present invention can be considered as encompassed within the field of medicine, particularly in the treatment of skin diseases.

STATE OF THE ART

Atopic dermatitis (AD) is a pruritic, inflammatory skin disease of chronic course, characterized by the development of lesions of eczema with a characteristic pattern of distribution that affects patients with cutaneous hyperreactivity to various environmental factors that are harmless to nonatopic patients. Atopic patients often have personal or family history of asthma or allergic rhinitis or AD, and have elevated IgE serum levels. Atopic dermatitis most often affects children, but can persist and/or onset may occur in adolescence or adulthood.

The prevalence of AD is between 4 and 20% of the population. There are great differences between rural or urban environments, the incidence being higher in the latter. The incidence of AD is probably increasing for the following reasons: Western lifestyle, increased maternal age, pollution, maternal smoking and reduced breastfeeding. Forty-five percent (45%) of children develop AD in the first six months of life and 85% in the first five years. When the disease starts in children under two years of age, 20% have persistent symptoms at the age of seven.

While atopic dermatitis is clinically manifest as eczema, both in its acute and chronic states, this disease presents great variability in: 1) the range of clinical manifestations; 2) the genetic basis of the same, and 3) the pathogenetic mechanisms underlying the clinical manifestations.

One of the most widespread hypotheses explaining the origin of atopic dermatitis speculates that it is one of a number of manifestations, affecting the skin in this case, of a systemic process involving other organs and systems of the human body, giving rise to a range of symptoms such as asthma, food allergy and allergic rhinitis, among others. In fact, a high percentage of patients with these diseases have elevated levels of IgE and eosinophils in peripheral blood although both the origin and clinical implications are unclear.

Regarding the pathophysiological mechanisms, the immune response is believed to play a major role in its origin. In fact, recent data implicate cutaneous dendritic cells (antigen-presenting cells) and the regulation of inflammatory-immune signals mediated by Th2 lymphocytes in the origin of the AD. The data indicate that the pathophysiological origin of AD can be found in these immunological mechanisms, involving both antigen-presenting cutaneous dendritic cells and immune regulation and inflammatory signals mediated by Th2 lymphocytes. What is not known at present is the source of the stimulus triggering the immunological cascade that occurs in AD.

The disease has a wide range of clinical manifestations ranging from minor forms such as hand eczema to more serious forms such as erythrodermic rash. There are no specific changes of pathological or laboratory type, therefore A D diagnosis is clinical and the standard diagnosis follows the Hanifin-Rajka criteria (Hanifin J M, et al. Acta Derm Venereol 1980; 92:44-7)

The clinical characteristics of AD are variable in relation to age and are included in the diagnostic criteria; they include itching, eczema lesions and lesions from scratching.

Itching: one of the most important and consistent findings of atopy. Atopic pruritus is intense and usually causes outbreaks. Itching causes patients to injure themselves by scratching. While the cause of pruritus is not well understood, it appears to be due to the release of inflammatory mediators and cytokines.

Eczema: eczema lesions may be acute and chronic. Acute injuries are characterized by macules, papules and erythematous, vesicular, exudative and very pruritic plaques. Repeated scratching and abrasions result in chronic injuries, which are characterized by manifest skin thickening accompanied by lichenification and with apparent presence of dry fibrous papules.

Lichenification: characteristically lichenified skin lesions are observed, consisting of not well-defined plaques with skin thickening displaying marked skin folds and lines Prurigo: small papules with a discreet bleb and marked galling that are the result of vigorous scratching.

Exfoliative dermatitis: cases of extensive atopy may clinically appear like generalized exfoliative dermatitis, included in the differential diagnosis of erythrodermas.

Besides establishing diagnosis, severity must be assessed or quantified. To this end, various methods and criteria have been developed to assess the severity and monitor response to treatment, in clinical trials and observational studies and even in clinical practice when the aim is to represent the patient's progress more accuracy than the description provided by the subjective perception of the patient, caregiver or doctor. In this respect, the most validated and used method is the so-called SCORAD index (Scoring Atopic Dermatitis) developed by the group European Task Force on Atopic Dermatitis in 1993 (European Task Force on Atopic Dermatitis. Severity scoring of atopic dermatitis: the SCORAD index.

Dermatology 1993; 186:23-31). It has proven to be the best method of assessing the severity of atopic dermatitis in comparative studies, and is also the most widely documented regarding validity, reproducibility, sensitivity and acceptability. The SCORAD is a scoring system that takes into account the extent and intensity of five types of basic AD lesions (erythema, edema/papule, oozing/crusting, excoriation and lichenification) and the symptoms (itching and loss of sleep).

There is some discrepancy regarding SCORAD index values that define the different degrees of severity. Some Spanish groups consider mild, moderate or severe correspond to the SCORAD index scores <25, 25 to 40 or >40, respectively, while other authors, based on correlations with laboratory tests, use the scores <20, 20 to 40 or >40, respectively to define mild, moderate and severe symptoms.

There is a consensus on the treatment of AD, aiming, in the first instance, to prevent itching and to eliminate the inflammatory lesion; and, secondly, to prevent relapses (Munoz F. 2002. JANO, 1432: 52-7; Boguniewitcz M, Schmid-Grendelmeier P, and Leung D Y M. 2006. J Allergy Clin Inmunol, 118: 40-3). To prevent itching and scratching, H1 antihistamines are prescribed, although effectiveness is not clearly demonstrated. The primary purpose of eczema treatment is to control the inflammatory lesion, which also helps control itching. Therefore topical corticosteroids of various strengths are used depending on the severity of the injury and the patient's condition. Those with apparently better results are traditional H1 antihistamines that cause sedation (hydroxyzine, clemastine, dexchlorpheniramine) and new-generation H1 antihistamines (dexfenfluramine, loratadine, cetirizine, and derivatives), which are less sedative but sometimes show results that do not differ with statistical significance from the placebo (Boguniewitcz M, et al 2006. Quoted ad supra).

Adverse effects of topical corticosteroids pose restrictions for use. Adverse reactions at the administration site are the most common. If applied periocularly, the following usually appear: skin atrophy, petechiae, atrophic striae, hypertrichosis, depigmentation, telangiectasia, folliculitis and glaucoma. Less frequently, more serious systemic adverse effects have also been described, such as the hypothalamic-pituitary adrenal-axis suppression, growth retardation or cushingoid.

Some patients' lack of response to corticosteroids and their adverse effects have triggered the development of new drugs to treat inflammation. Among the best studied are topical calcineurin inhibitors (tacrolimus and pimecrolimus) Leung, D Y M and Bleder, T. 2003, Lancet, 361: 151-60; Munoz, F. 2002, JANO, 1432: 52-7). However, there are still doubts about the safety of these drugs in long-term treatments. In fact, the prospectus of products containing tacrolimus or pimecrolimus for topical treatment of atopic dermatitis indicate they should only be used in children over two years of age for whom the use of topical corticosteroids is not recommended or has previously failed.

The use of probiotics to treat AD has been studied in recent years in a limited number of pilot studies and results differ depending on the probiotic used and the age of patients in the trial (Soo-Pk Kim, et al. 2014. Ann Allergy Asthma Immunol. 113: 217e226; Gerasimov, S V et al. 2010. Am J Clin Dermatol, 11:351e361; Farid, R. et al. 2011. Iran J Pediatr. 21:225e230). The most recent studies, including a meta-analysis of previous publications, demonstrate the beneficial effect of probiotic use in certain circumstances related to age, bacterial strain or combination of probiotics and dose used ((Farid, R. et al 2011 cited ad supra; Van del Aa L B, et al. 2010. Clin Exp Allergy. 40:795e804; Boyle, R J et al. 2008. Cochrane Database Syst Rev, 4: CD006135: Lee, J. et al. 2008. J Allegy Clin Immunol. 121:116). The probiotics most studied terms of treating atopic dermatitis and preventing new outbreaks of the disease belong to the genera *Bifidobacterium* and *Lactobacillus*, as these seem to yield better results (Lee, J. et al. 2008. Quoted ad supra).

There is a well-known medical need to develop treatments of quality, that are safe and effective for the long-term treatment of AD, since atopic dermatitis affects an importance proportion of the population, with notable effects on their quality of life, which may be affected by medical complications, etc. Topical corticosteroids are considered to be a very effective treatment, but imply a high risk of adverse effects. The incorporation of new alternatives to topical corticosteroids (such as calcineurin inhibitors) responds to this need, although the risk of adverse effects with these new drugs has yet to be defined. Therefore, the prior art shows there is the need to develop new compositions that are useful in treating AD, which prove to be effective and lack the typical side effects of the drugs used to date.

DETAILED DESCRIPTION OF THE INVENTION

The authors of the present invention have discovered that administering a probiotic composition that modifies the intestinal microbiota to an individual suffering from atopic dermatitis, together with the usual treatment, surprisingly allows remission and/or improvement of the evolution of outbreaks of atopic dermatitis in the individual. As shown in the examples accompanying the present description, when the probiotic composition (comprising microorganisms of the genera *Bifidobacterium* and *Lactobacillus*) was administered together with the usual chronic treatment of patients with outbreaks of atopic dermatitis, an improvement in the SCORAD index of 82.36% was observed while the improvement in this index in the cases treated with the usual chronic treatment but without the probiotic composition was 28.4%, differences considered clinically and statistically significant. Moreover, the improvement produced by the probiotic composition occurred since the first month of intake, maintaining or increasing the differences in subsequent analysis for 2 and 3 months of treatment. Additionally, another advantage of treating AD with the probiotic composition of the invention is that corticosteroid use by patients in the group treated with said probiotic composition was lower than in the group receiving placebo.

In addition to this beneficial effect on disease progression in patients with an outbreak of atopis dermatitis, it was also observed that in the three months after discontinuation of treatment with the above-mentioned probiotic composition, individuals who had received treatment with said composition had fewer outbreaks and longer disease-free time-lapses than those patients who had not received treatment.

Thus the utility of the probiotic composition described herein for the treatment and/or prevention of atopic dermatitis is demonstrated.

The inventors have developed a number of inventive aspects that will be described in detail below.

Composition of the Probiotic Composition of the Invention and its Use in the Treatment of Atopic Dermatitis (AD).

In one aspect, the present invention relates to a probiotic composition that comprises microorganisms of *Bifidobacterium animalis* subs. *lactis* (hereinafter *B. lactis*), *Bifidobacterium longum* and *Lactobacillus casei*.

In the present invention the term "probiotic composition" is that composition comprising at least one microorganism which, when ingested, interacts with the individual's metabolism and produces a beneficial effect in the same. In the present invention, the probiotic composition comprises the microorganisms *B. lactis, B. longum* and *L. casei*, hereinafter, "probiotic composition of the invention".

*B. lactis* is a bacterium commonly used as a probiotic, found mostly in yogurt and other dairy products, including infant formula. The scientific classification of *B. lactis* is: Kingdom: Bacteria Division: Firmicutes Class: Actinobacteria, Order: Bifidobacteria, Family: Bifidobacteriaceae, Genus: *Bifidobacterium*, Species: *Bifidobacterium animalis* subsp. *lactis*.

*L. casei* is a bacterium commonly used as a probiotic, found mostly in yogurt and other dairy products, including infant formula. The scientific classification of *L. casei* is: Kingdom: Bacteria Division: Firmicutes Class: Bacilli Order: Lactobacillales, Family: Lactobacillaceae, Genus: *Lactobacillus*, Species: *Lactobacillus casei*.

Moreover, *B. longum* is a Gram negative, catalase-negative bacterium, rounded in shape, located in the gastrointestinal tract, where it produces lactic acid. The scientific classification of *B. longum* is: Kingdom: Bacteria Division: Firmicutes Class: Actinobacteria, Order: Bifidobacteria, Family: Bifidobacteriaceae, Genus: *Bifidobacterium*, Species: *Bifidobacterium longum*.

In a particular embodiment, the probiotic composition of the invention comprises *B. lactis* CECT 8145 (and/or strains derived therefrom), *B. longum* CECT 7347 (and/or strains derived therefrom) and/or *L. casei* CECT 9104 (and/or strains derived therefrom).

*B. lactis* strain CECT 8145 was isolated from feces of a healthy breastfeeding child less than three (3) months old. This strain was deposited on 14 May 2012 under the Budapest Treaty in the Spanish Type Culture Collection as an International Depositary Authority (based in Building 3 CUE, Parc Cientific Universitat de Valencia, C/Catedrático Agustin Escardino, 9, 46980 Paterna (Valencia) SPAIN). The deposit number assigned is CECT 8145.

*L. casei* strain CECT 9104 was isolated from feces of a healthy and breastfeeding child less than three (3) months old. This strain was deposited on 25 Feb. 2016 under the Budapest Treaty in the Spanish Type Culture Collection as an International Depositary Authority (based in Building 3 CUE, Parc Cientific Universitat de Valencia, C/Catedrático Agustin Escardino, 9, 46980 Paterna (Valencia) SPAIN). The deposit number assigned was CECT 9104.

*B. longum* strain CECT 7347 was isolated from feces of a healthy breastfeeding child less than three (3) months old and deposited on 20 Dec. 2007 under the Budapest Treaty in the Spanish Type Culture Collection as the International Depository Authority (based in Building 3 CUE, Parc Cientific Universitat de Valencia, C/Catedrático Agustin Escardino, 9, 46980 Paterna (Valencia) SPAIN). The deposit number assigned was CECT 7347.

The present invention also contemplates those microorganisms or bacteria derived from the microorganisms *B. lactis, B. longum* and *L. casei* (or their corresponding strains *B. lactis* CECT 8145, *L. casei* CECT 9104 and *B. longum* CECT 7347) and that may be part of the probiotic composition of the invention as they retain the ability to reduce and/or improve the evolution of atopic dermatitis in individuals who suffer this pathology. Examples of strains or microorganisms derived from strains comprised within the probiotic composition of the invention may be mutants and genetically modified organisms which show variations in their genome compared to the genome of the strains of the invention, but which do not affect the ability of strains to reduce and/or improve the evolution of atopic dermatitis in the individual. Strains derived from *B. lactis, B. longum* and *L. casei* (or from strains of *B. lactis* CECT 8145, *L. casei* CECT 9104 and *B. longum* CECT 7347) can be naturally or intentionally produced by mutagenesis, as known in the art, such as for example, but not limited to, the growth of the parent strain in the presence of mutagenic agents or stressors or by genetic engineering directed to the modification, deletion and/or insertion of specific genes. Thus, as indicated above, the present invention also contemplates genetically modified organisms derived from *B. lactis, B. longum* and *L. casei* (or from strains of *B. lactis* CECT 8145, *L. casei* CECT 9104 and *B. longum* CECT 7347), that retain the ability to reduce and/or improve the evolution of atopic dermatitis in an individual and, therefore, to be used in the treatment of atopic dermatitis. An example of a test to verify if an organism has the ability to reduce and/or improve the evolution of atopic dermatitis in an individual is described in the accompanying examples herein.

Furthermore, the present invention, also contemplates cellular components, metabolites and molecules secreted by *B. lactis, B. longum* and *L. casei* or their corresponding strains *B. lactis* CECT 8145, *L. casei* CECT 9104 and/or *B. longum* CECT 7347 as well as compositions comprising said components, be they cells, metabolites or secreted molecules, and uses thereof for the treatment and/or prevention of atopic dermatitis. The cellular components of bacteria could include components of the cell wall (such as, but not limited to, peptidoglycan), nucleic acids, membrane components and other, such as proteins, lipids and carbohydrates and combinations thereof (such as lipoproteins, glycolipids or glycoproteins). Metabolites include any molecule produced or modified by the bacterium as a result of its metabolic activity during growth, its use in technological processes or during storage of the product (probiotic composition of the invention). Examples of these metabolites include, but are not limited to, organic and inorganic acids, proteins, peptides, amino acids, enzymes, lipids, carbohydrates, lipoproteins, glycolipids, glycoproteins, vitamins, salts, minerals and nucleic acids. Secreted molecules include any molecule secreted or released to the outside by the bacterium during growth, its use in technological processes (for example, food processing or drugs) or during storage of the product (the probiotic composition of the invention). Examples of these molecules include, but are not limited to, organic and inorganic acids, proteins, peptides, amino acids, enzymes, lipids, carbohydrates, lipoproteins, glycolipids, glycoproteins, vitamins, salts, minerals and nucleic acids.

As understood by experts in the art, the probiotic composition of the invention may be formulated for pharmaceutical administration, i.e., forming part of pharmaceutical products to be administered to the subject (for example orally, topically, etc.), and/or for food administration, i.e. forming part of the foods consumed in the subject's diet. In the present invention, said composition is for use to diminish, reduce, treat and/or prevent atopic dermatitis. Therefore, in a particular embodiment, the probiotic composition of the invention is a pharmaceutical composition and/or a nutritional composition.

The pharmaceutical composition is a set of components or compounds which is formed at least by microorganisms *B. lactis, L. casei* and *B. longum*, in particular by strains of *B. lactis* CECT 8145, and/or *L. casei* CECT 9104 and/or *B. longum* CECT 7347 (or strains derived therefrom) at any concentration and which additionally may comprise one or more components or compounds having any biological, pharmacological and/or veterinary activity which, upon administration to a subject, may further increase, enhance and/or promote the activity of the strains included in the probiotic composition of the invention. As understood by one skilled in the art, the additional components or compounds must be compatible with the strains of the probiotic composition of the invention. In the context of the present invention, the term "pharmaceutical composition" also encompasses veterinary compositions.

Examples of useful components or compounds used in the treatment of atopic dermatitis which can be part of the pharmaceutical composition include, but are not limited to, traditional H1 antihistamines (e.g. hydroxyzine, clemastine and dexchlorpheniramine), recently developed H1 antihistamines (e.g. dexfenfluramine, loratadine, cetirizine, and derivatives) and calcineurin inhibitors (e.g. tacrolimus and pimecrolimus).

In a particular embodiment, the pharmaceutical composition further comprises a pharmaceutically acceptable carrier and/or excipient.

The term "excipient" refers to a substance that helps the absorption of any components or compounds of the probiotic composition of the invention, namely, of strains of the invention, or stabilizes the components or compounds and/or assists the preparation of the pharmaceutical composition in the sense of giving it consistency or flavors to make it more pleasant. Thus, the excipients may have the function, by way of example but not limited thereto, of binding the components (for example, starches, sugars or cellulose), sweetening, coloring, protecting the active ingredient (for example, to insulate it from air and/or moisture), filling a pill, capsule or any other presentation or a disintegrating function to facilitate dissolution of the components, without excluding other excipients not listed in this paragraph. Therefore, the term "excipient" is defined as a material, included in the galenic forms, which is added to the active ingredients or their associations to enable their preparation and stability, modify their organoleptic properties and/or determine the physico-chemical properties of the pharmaceutical composition and its bioavailability. The "pharmaceutically acceptable" excipient must allow the activity of components or compounds of the pharmaceutical composition, that is, must be compatible with the strains of the invention.

The "galenic form" or "pharmaceutic form" is the configuration to which the active ingredients and excipients are adapted to provide a pharmaceutical composition or a drug. It is defined by the combination of the form in which the pharmaceutical composition is presented by the manufacturer and the form in which it is administered.

The "vehicle" or "carrier" is preferably an inert substance. Carrier functions are to facilitate the incorporation of other components or compounds, allow better dosage and/or administration and/or give consistency and form to the pharmaceutical composition. Therefore, the carrier is a substance used in the drug to dilute any of the components or compounds of the pharmaceutical composition of the present invention to a given volume or weight; or that even without diluting these components or compounds, it is able to allow better dosage and administration and/or give consistency and form to the drug. When the presentation is liquid, the pharmaceutically acceptable carrier is the diluent. The carrier can be natural or unnatural. Examples of pharmaceutically acceptable carriers include, without being limited thereto, water, salt solutions, alcohol, vegetable oils, polyethylene glycols, gelatine, lactose, starch, amylose, magnesium stearate, talc, surfactants, silicic acid, viscous paraffin, perfume oil, monoglycerides and diglycerides of fatty acids, fatty acid esters petroetrals, hydroxymethylcellulose, polyvinylpyrrolidone and the like.

Furthermore, the excipient and the carrier must be pharmacologically acceptable, i.e., the excipient and the carrier are permitted and evaluated so as not to cause damage to the subject to whom it is administered. Additionally, the carrier and/or vehicle can be natural, i.e., naturally occurring, or unnatural, that is, they may or may not occur or in nature but, if they are in nature, are not naturally found in combination with the strains of the invention.

In each case the presentation of the pharmaceutical composition will be adapted to the type of administration used. Thus, the composition may be presented in the form of solutions or any other form of clinically permissible administration and in a therapeutically effective amount. The pharmaceutical composition can be formulated into solid, semisolid or liquid preparations, such as tablets, capsules, powders, granules, solutions, suppositories, gels or microspheres. In a particular embodiment, the pharmaceutical composition is formulated for administration in liquid form or in solid form.

In another particular embodiment, the solid formulation is selected from the group consisting of tablets, lozenges, sweets, chewable tablets, chewing gums, capsules, sachets, powders, granules, coated particles or coated tablets, tablet, pills, troches, gastro-resistant tablets and capsules and dispersible strips and/or films.

In another particular embodiment, the liquid formulation is selected from the group consisting of oral solutions, suspensions, emulsions and syrups.

Likewise, various systems are known that can be used for sustained-release administration of the probiotic composition of the invention, including, for example, the encapsulation in liposomes, microbubbles, microparticles or microcapsules and the like, of the same. The suitable sustained-release forms as well as materials and methods for their preparation are well known in the state of the art. Thus, the orally administrable form of the probiotic composition of the invention is in a sustained-release form further comprising at least one coating or matrix. The sustained release coating or matrix includes, without limitation to, natural semisynthetic or synthetic polymers, water-insoluble or modified, waxes, fats, fatty alcohols, fatty acids, natural, semisynthetic or synthetic plasticizers or a combination of two or more of all the above-mentioned. Enteric coatings can be applied using conventional processes known to those skilled in the art.

In addition to what has been described above, the present invention also encompasses the possibility that the probiotic composition of the invention may be administered to a subject together with other components or compounds, although these are not part of the probiotic composition. Examples of such components or compounds have been mentioned in preceding paragraphs.

In the event that the probiotic composition of the invention is formulated as a nutritional composition, said nutritional composition may be a food or be incorporated into a food or food product intended for both human and animal consumption. Thus, in a particular embodiment, the nutritional composition is selected from between a food (which may be a food for specific nutritional purposes or medicinal food) and a nutritional supplement.

In the present invention, the term "nutritional composition" refers to that food, which regardless of providing nutrients to the subject who consumes it, beneficially affects one or more bodily functions, so as to bestow upon said subject better health and wellness. In the present invention, said nutritional composition is intended to ease, reduce, treat and/or prevent atopic dermatitis.

The term "supplement", synonymous with any of the terms "dietary supplement", "nutritional supplement", "food supplement", or "alimentary supplement" or "alimentary complement" refers to products or preparations whose purpose is to supplement the normal diet consisting of sources of concentrated nutrients or other substances with a nutritional or physiological effect on the subject. In the present invention, the "substance" which has a nutritional or physiological effect on the individual when the food complement is ingested are the microorganisms *B. lactis, L. casei* and *B. longum*, in particular the strains *B. lactis* CECT 8145, and/or *L. casei* CECT 9104 and/or *B. longum* CECT 7347, which are part of the probiotic composition of the invention. The food supplement may be in single or combined form, and may be marketed in dosage form, i.e. in capsules, pills, tablets and other similar forms, sachets of powder, ampoules of liquids and drop dispensing bottles and other similar forms such as liquids and powders designed to be taken in a single dose.

There is a wide range of nutrients and other elements that may be present in dietary complements including, but not limited to, vitamins, minerals, amino acids, essential fatty acids, fiber, enzymes, plants and plant extracts. Since their role is to complement the supply of nutrients in a diet, they should not be used as a substitute for a balanced diet and intake should not exceed the daily dose expressly recommended by the doctor or nutritionist. The probiotic composition can also be part of the so-called "food for special groups", i.e. foods that meet specific nutritional needs.

Examples of foods that may comprise the probiotic composition of the invention (microorganisms *B. lactis, L. casei* and *B. longum,* in particular strains *B. lactis* CECT 8145, and/or *L. casei* CECT 9104 and/or *B. longum* CECT 7347 (or strains derived therefrom)) include, but are not limited to, feed, dairy products, vegetable products, meat products, snacks, chocolates, drinks, baby food, cereals, fried foods, industrial bakery products and biscuits. Examples of milk products include, but are not limited to, products derived from fermented milk (for example, but not limited to, yogurt or cheese) or non-fermented milk (for example, but not limited to, ice cream, butter, margarine or whey). The vegetable product is, for example, but not limited to, a cereal in any form of presentation, fermented (for example, but not limited to, soy yogurt or oat yogurt) or unfermented, and a snack. The beverage may be, but is not limited to, non-fermented milk. In a particular embodiment, the food product or food is selected from the group consisting of fruit or vegetable juices, ice cream, infant formula, milk, yogurt, cheese, fermented milk, powdered milk, cereals, baked goods, milk-based products, meat products and beverages.

Additionally, the probiotic composition of the invention may comprise other microorganisms in addition to *B. lactis, L. casei* and *B. longum,* in particular strains *B. lactis* CECT 8145, and/or *L. casei* CECT 9104 and/or *B. longum* CECT 7347. Thus, in a particular embodiment, the probiotic composition of the invention further comprises a microorganism selected from the group consisting of *Lactobacillus* sp., *Streptococcus* sp., *Bifidobacterium* sp., *Saccharomyces* sp., *Kluyveromyces* sp. and combinations thereof.

In another even more particular embodiment, the *Lactobacillus* sp. is *L. rhamnosus, L. delbrueckii* subsp. *bulgaricus, L. kefir, L. parakefir, L. brevis, L. casei, L. plantarum, L. fermentum, L. paracasei, L. acidophilus, L. paraplantarum* or *L. reuteri; Streptococcus* sp. is St. *thermophilus; Bifidobacterium* sp. is *B. longum, B. breve, B. bifidum, B. catenulatum, B. adolescentis* or *B. pseudocatenulatum; Saccharomyces* is *S. cerevisiae* or *S. boulardii*; or *Kluyveromyces* sp. is *K. lactis* or *K. marxianus.*

In another particular embodiment, the probiotic composition of the invention is administered to a subject through the diet.

As understood by one skilled in the art, the microorganisms *B. lactis, L. casei* and *B. longum,* in particular the strains *B. lactis* CECT 8145, *L. casei* CECT 9104 and/or *B. longum* CECT 7347, have to be present in the probiotic composition of the invention in a therapeutically effective amount so that they can exert their effect of easing, reducing, treating and/or preventing atopic dermatitis.

In the present invention "therapeutically effective amount" is that amount of the component or compound of the pharmaceutical composition, which when administered to a subject, is sufficient to produce the desired effect. Said component or compound of the pharmaceutical composition refers to the microorganisms *B. lactis, L. casei* and *B. longum,* in particular the strains *B. lactis* CECT 8145, *L. casei* CECT 9104 and/or *B. longum* CECT 7347. As known by experts in the matter, the therapeutically effective amount may vary depending on, for example, age, body weight, general health, sex and diet of the subject, as well as according to the mode and time of administration, excretion rate or drug combination, among other factors.

Thus, in a particular embodiment, the total concentration of microorganisms of *B. lactis, L. casei* and *B. longum,* in particular the strains *B. lactis* CECT 8145, and/or *L. casei* CECT 9104 and/or *B. longum* CECT 7347 in the composition is between $10^3$ and $10^{12}$ cfu, preferably $10^9$ cfu. In another particular embodiment, the dose of administration of microorganisms *B. lactis, L. casei* and *B. longum,* in particular *B. lactis* CECT 8145, *L. casei* CECT 9104 and/or *B. longum* CECT 7347, in the composition is between $10^6$ and $10^{12}$ cfu/day, preferably $10^9$ cfu/day, and in another even more particular embodiment, the administration regime is at least once daily, in particular twice daily, and more in particular, three times a day, one with each food intake (breakfast, lunch and dinner).

In another particular embodiment, the concentration of *B. longum,* particularly *B. longum* strain CECT 7347, with respect to the total concentration of microorganisms present in the composition is selected from any of the following values: 10%, 15%, 20%, 25%, 30%, 35%, 40%, 45%, 50%, 55%, 60%, 65%, 70%, 75% or 80%. In another particular embodiment, the concentration of *B. lactis,* particularly *B. lactis* strain CECT 8145, with respect to the total concentration of microorganisms present in the composition is selected from any of the following values: 10%, 15%, 20%, 25%, 30%, 35%, 40%, 45%, 50%, 55%, 60%, 65%, 70%, 75% or 80%. In another particular embodiment, the concentration *L. casei* in particular *L. casei* strain CECT 9104, with respect to the total concentration of microorganisms present in the composition is selected from any of the following values: 10%, 15%, 20%, 25%, 30%, 35%, 40%, 45%, 50%, 55%, 60%, 65%, 70%, 75% or 80%. As understood the by the expert, the composition of the invention comprises any combination of the concentrations for each of the microorganisms described above.

In another particular embodiment, the concentration of *B. longum* with respect to the total concentration of microorganisms present in the composition is at least between 25% and 45%, preferably at least 35%; *B. lactis* concentration with respect to the total concentration of microorganisms is at least between 25% and 45%, preferably at least 35%; and/or *L. casei* concentration with respect to the total concentration of microorganisms is between 20% and 40%, preferably 30%.

The probiotic composition of the invention is useful in the treatment and/or prevention of atopic dermatitis in an individual, as well as improving the evolution of atopic dermatitis once intake of the probiotic composition described herein is suspended.

Thus, another object described herein relates to the probiotic composition described herein for use as a drug.

The term "drug", as used herein, refers to any substance used for prevention, diagnosis, alleviation, treatment or cure of diseases in humans and animals. In the context of the present invention the disease is AD.

Another object herein described relates to probiotic composition such as described above, in the treatment and/or prevention of AD in an individual suffering from this disease.

In the present invention the term "subject" is equivalent to the term "individual"; so both terms can be used interchangeably herein. "Subject" means, in addition to any individual, any animal belonging to any species. Examples of subjects include, but are not limited to, animals of commercial interest such as birds (hens, ostriches, chicks, geese, partridges, etc.); rabbits, hares, pets (dogs, cats, etc.); sheep, goat cattle (goats, etc.); swine (boars, pigs, etc.); equine livestock (horses, ponies, etc.); cattle (bulls, cows, oxen, etc.); animals of hunting interest, such as stags, deer, reindeer, etc.; and humans. However, in a particular embodiment, the subject is a mammal, preferably the mammal is a human being of any race, sex or age.

In the present invention the term "prevention" means to avoid occurrence of the disease or pathological condition in an individual, particularly when the individual has predisposition for the pathological condition, but has not yet been diagnosed. In the present invention, the disease or pathological condition is an outbreak of atopic dermatitis.

In the present invention, the term "treat" or "treatment" comprises inhibiting the disease or pathological condition, i.e., stopping its development; relieving the disease or pathological condition, i.e., causing regression of the disease or pathological condition; and/or stabilizing the disease or pathological condition in an individual. In the present invention, the disease or pathological condition is atopic dermatitis.

In the present invention the term "atopic dermatitis" (AD) is understood as inflammatory dermatoses, pruritic, chronic course, characterized by the development of lesions of eczema with a characteristic pattern of distribution that affects individuals with cutaneous hyper-reactivity to various environmental factors that are harmless for non-atopic individuals. Being a chronic inflammatory process there are outbreaks of inflammatory nature due to for this great skin hyperactivity causing lesions both in skinfold areas and in areas of extension, following a pattern of acute or subacute eczema. Atopic dermatosis may manifest in many forms and places other than the skin.

Method of Treatment and/or Prevention of Inflammatory Skin Diseases

Another aspect, the invention relates to a method for the treatment of atopic dermatitis in a subject, hereinafter, method of treatment of the invention, comprising the administration of the probiotic composition described in the present invention to an individual who presents atopic dermatitis.

All particular terms, definitions and embodiments of previous inventive aspects are applicable to the treatment method of the invention.

Throughout the description and claims the word "comprise" and its variants are not intended to exclude other technical characteristics, additives, components or steps. For those skilled in the art, other objects, advantages and characteristics of the invention will become apparent, in part, from the description and, partly, from putting into practice the invention. The following examples and figures are provided by way of illustration and are not intended to limit the scope of the present invention.

BRIEF DESCRIPTION OF THE FIGURES

FIG. 6 shows the results of SCORAD index a month after starting treatment with the probiotic composition of the invention or placebo. The results show the absolute value of SCORAD for each treatment group (FIG. 6A) and the % reduction in the SCORAD index during the course of treatment in both groups (FIG. 6B). V3, check-up at 1 month. Group A, group consuming the placebo; Group B, group consuming the probiotic composition.

FIG. 7 shows the SCORAD index results within two months of starting treatment with the probiotic composition of the invention or placebo. The results show the absolute value of SCORAD for each treatment group (FIG. 7A) and SCORAD % reduction during the course of treatment in both groups (FIG. 7B). V5, check-up month 2. Group A, group consuming the placebo; Group B, group consuming the probiotic composition.

FIG. 8 shows the results of SCORAD index three months (end of trial) after starting treatment with the probiotic composition of the invention or placebo. The results show the absolute value of SCORAD in each treatment group (FIG. 8A) and SCORAD % reduction in both groups during the treatment time (FIG. 8B). V7, check-up at 3 months. Group A, group consuming placebo; Group B, group consuming the probiotic composition.

EXAMPLES

Figure 1:
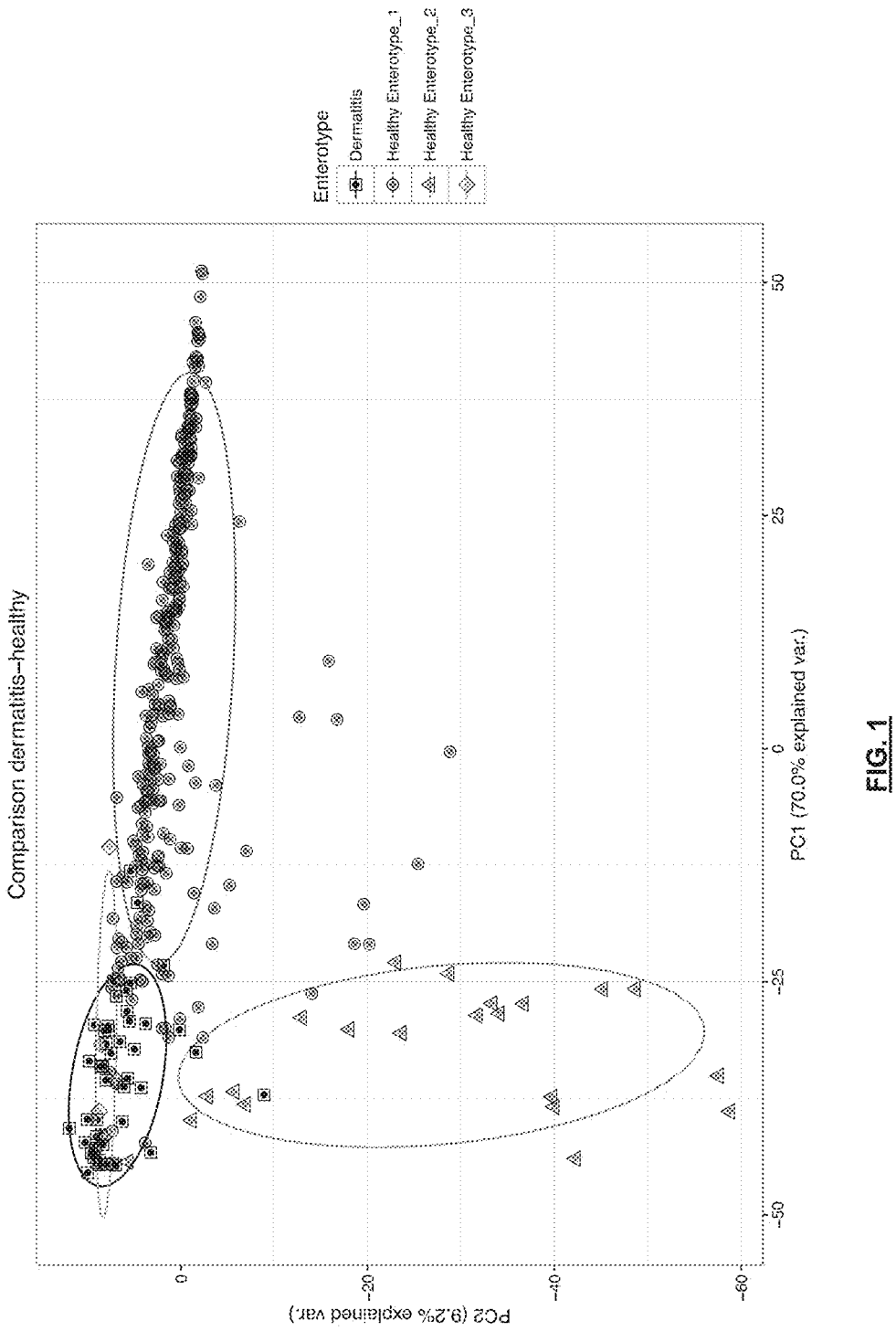
FIG. 1 is a diagram showing the analysis of the main components of the microbiological profiles of stool samples taken from patients with atopic dermatitis (square symbol and black) compared to healthy individuals belonging to enterotype 1 (circular symbol and dark gray), to enterotype 2 (triangular symbol and gray) and to enterotipo3 (rhombic symbol and light gray).

The invention will be illustrated by tests performed by the inventors, which show the properties of the probiotic composition of the invention.

Example 1: Determination of Bacterial Microbiota in Patients with AD 1.1 Material and Methods Based on the stool samples of 49 patients with dermatitis, extraction of genetic material (DNA) was performed using a combination of mechanical and enzymatic disruption of cell walls and membranes in order to increase the yield of extraction and not bias the presence of bacteria with cell wall (Gram+). The genetic material obtained by extraction was measured to assess quality and quantity using a Nanodrop 2000 ThermoScientific to inspect ratios 260/280 and 260/230 indicating the extraction quality (presence of PCR inhibitors, pigment, etc.). Later, after verifying the quality of the same, massive sequencing libraries were conducted, capturing the hypervariable region V3-V4 of the bacterial 16s rRNA gene (based on Klindworth A, et al. (2013) Nucleic Acids Res 41: el) according to the protocol described by Illumina for analysis of the microbial composition based on the capture of 16s rRNA. Each library was quantified with Quant-iT PicoGreen by Invitrogen and mixed equimolarly for subsequent sequencing.

Samples were sequenced in MiSeq platform in a combination of 300 "Paired-End" cycles. The resulting FASTQ files were treated to ensure high quality sequence analysis. For this purpose, a quality control was conducted consisting of:

1. Joining the ends to reconstruct unique sequences using the program 'pear' v0.9.6. (Zhang J, et al (2014) Bioinformatics 30 (5):614-20).
2. Elimination of sequencing adapters and capture primers from the hypervariable regions V3 and V4 with the program cutadapt version 1.9.1. (Martin M (2010) EMBnet.journal [S.L.], 17 (1): 10-12. ISSN 2226-6089.).
3. Elimination of low quality sequences using FASTX-ToolKit version 0.91.

4. Elimination of chimeras produced by PCR using the UCHIME program (December 2015) (Edgar R C, et al (2011) Aug. 15; 27 (16): 2194-200) and the last database of chimeras.

The resulting samples were compared against a sequence database of 16S rRNA (NCBI) using a BLAST type local alignment (Altschul S F, et al (1990) J. Mol Biol. 215: 403-410).

Each of the sequences for which a score was obtained of ninety-five percent (95%) identity was inspected at different taxonomic of levels: Phylum, Family, Genus and Species.

The R statistical package was used for statistics, to construct graphs for principal component analysis (PCA).

It is interesting to note that there is great variation in microbial populations of the digestive tract of each individual, epidemiological studies suggest that the microbiota of almost all of them can be classified as belonging to three distinct categories known as enterotypes (Arumugam et al., (2011) Nature 473:174-180). This classification is based on the predominance in each of these three enterotypes of members of the genera *Bacteroides, Prevotella* or Ruminococcus. Enterotype 1 (ent1) is referred to when the *Bacteroides* genus is predominant, enterotype 2 (ent2) if the *Prevotella* genus is predominant and enterotype 3 (ent3) when the Ruminococcus genus is predominant (Dave et al., (2012). Trans. Res. 160, 246-257).

II. Results

As mentioned above, the microbial composition was analyzed in stool samples from individuals suffering from atopic dermatitis as compared to stool samples from healthy individuals.

The results show that, as can be seen in FIG. 1, microbiological profiles of samples from patients with AD are closer to healthy individuals with enterotype 3 than to the other healthy individuals. As shown top left of the above-mentioned FIG. 1, the patients with AD (quadricular and black symbol) cluster together with healthy individuals with enterotype 3 (rhombic and light gray symbol), but with greater dispersion in the case of AD patients than in healthy individuals with enterotype 3. By contrast, individuals in the healthy population with enterotype 1 (circular and dark gray symbol) or enterotype 2 (triangular and gray symbol) cluster in the part top, from left to right, and on the left side, top down, respectively. It is also noticeable that samples clustering on the right-hand side of the graph have a greater abundance of the *Bacteroides* genus and fewer *Prevotella* and *Faecalibacterium*, while samples clustering at the top of the graph in FIG. 1 present a clear absence of *Prevotella*; hence samples from healthy patients with enterotype 2 (greater abundance of species of the *Prevotella* genus) are located in the lower left-hand corner and show an increase in *Faecalibacterium* and Ruminococcus. These data enable us to state that the microbiome of patients with AD is closer to that of healthy individuals with enterotype 3, but with a different composition and microbial variability.

Figure 2:
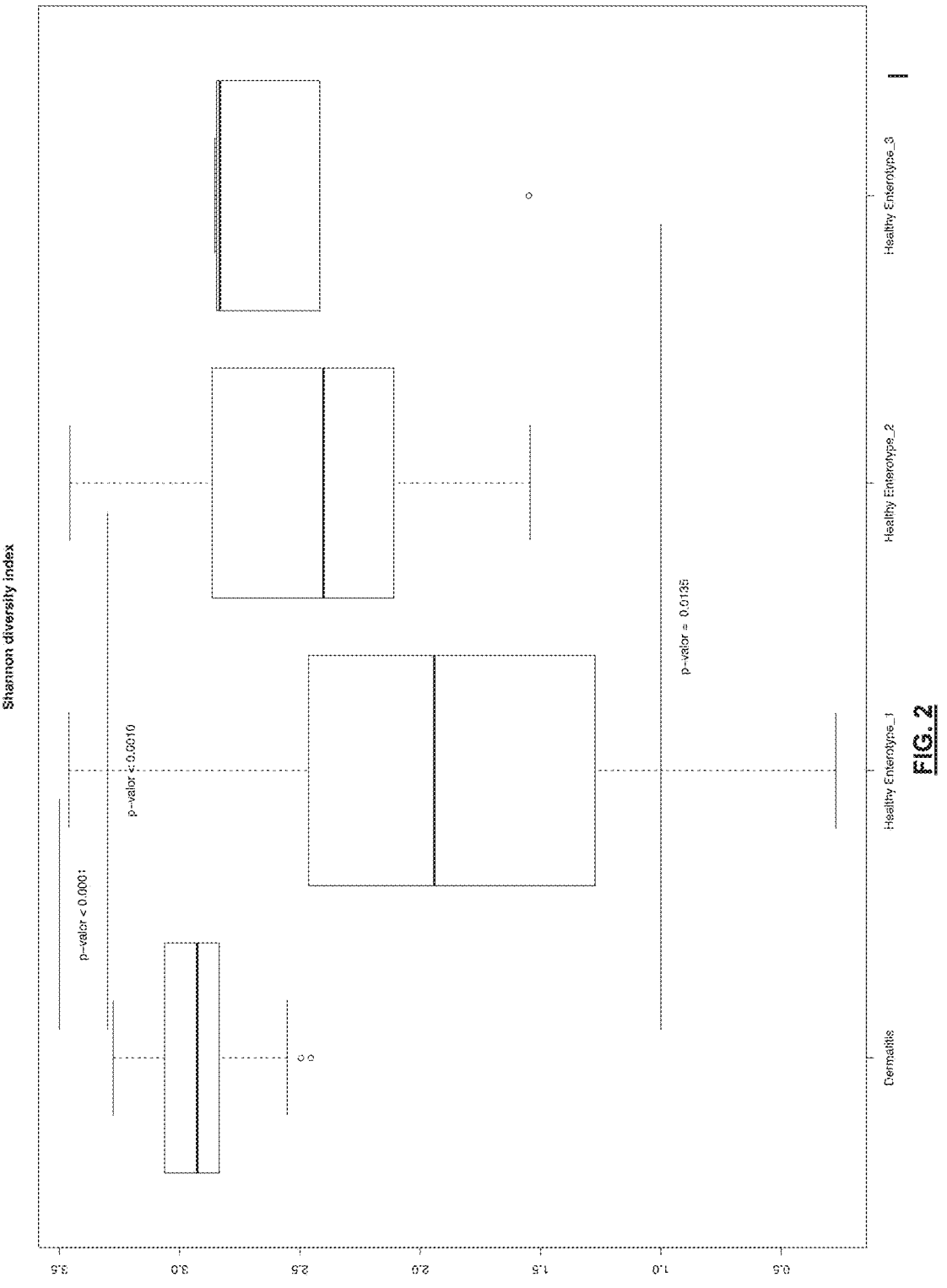
FIG. 2 is a diagram showing the variability analysis of stool samples of patients with dermatitis compared with the healthy population in each of the enterotypes. The figure shows statistical significances after applying a Wilcoxon test.

This different variability and microbial composition among healthy individuals with enterotype 3 and AD patients is noticeable in greater detail when the variability of bacterial populations is analyzed in samples of the healthy population (with each of the three separate enterotypes) for samples of patients with AD by Shannon index (FIG. 2). As shown in FIG. 2, in general, patients with AD have greater variability compared to healthy individuals, having a median and interquartile range of 2.97 (2.84 to 3.06) for patients with atopic dermatitis and 1.99 (1.37 to 2.52); 2.14 (1.50 to 2.62) and 2.23 (1.91 to 2.57) for healthy individuals with enterotypes 1, 2 and 3, respectively. Specifically, AD patients have a significantly higher bacterial variability than that present in any of the enterotypes of healthy individuals, because in all cases p<0.0001 on comparing the microbial variability of AD patients with that of the healthy population with different enterotypes.

In order to determine the bacteria that differentiate the healthy population from the population with atopic dermatitis, we proceeded to classify patients with atopic dermatitis based on the predominance of *Bacteroides* (ent1), *Prevotella* (ent2) or Ruminococcus (ent3). Subsequently, we examined whether there were differences between each of the different enterotypes of the healthy population regarding the different enterotypes in people with AD. Firstly, from the total of 49 patients with AD, 25 were classified as ent1; two as ent2; and 22 as ent3. Similarly, of the 324 healthy subjects, 298 were classified as ent1; 21 as ent2; and five as ent3. Then bacterial variability was analyzed within each enterotype, 1, 2 or 3 among AD patients as compared to healthy subjects.

Figure 3:
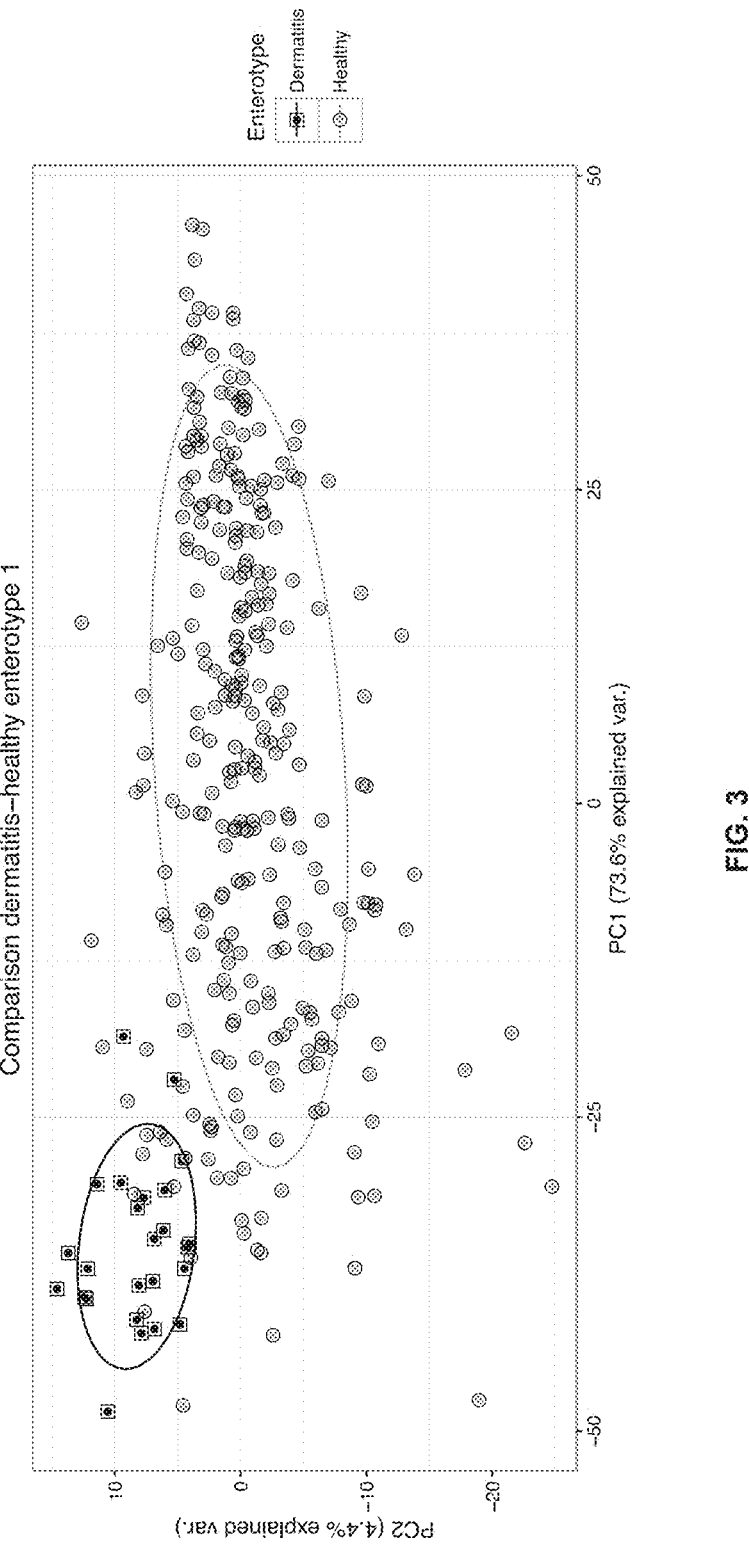
FIG. 3 is a diagram showing the principal components analysis of patients with dermatitis or classified as belonging enterotype 1 (square symbol and black) compared to samples from healthy population of enterotype 1 (circular symbol and gray). The genres most represented in the samples located in the upper right part of the figure shown in black and those who are under-represented in this situation are shown in gray. With respect to the samples located in the lower left corner, the trend is the opposite: the less abundant are marked in black while the abundant are marked in gray.

FIG. 3 shows the bacterial variability among healthy subjects versus patients with AD, all with enterotype 1. As shown in FIG. 3, healthy individuals have greater abundance of *Bacteroides* than AD patients, while patients with AD display greater abundance of the genera *Faecalibacterium, Bifidobacterium* and, especially, low abundance of species of the genus *Alistipes*.

Figure 4:
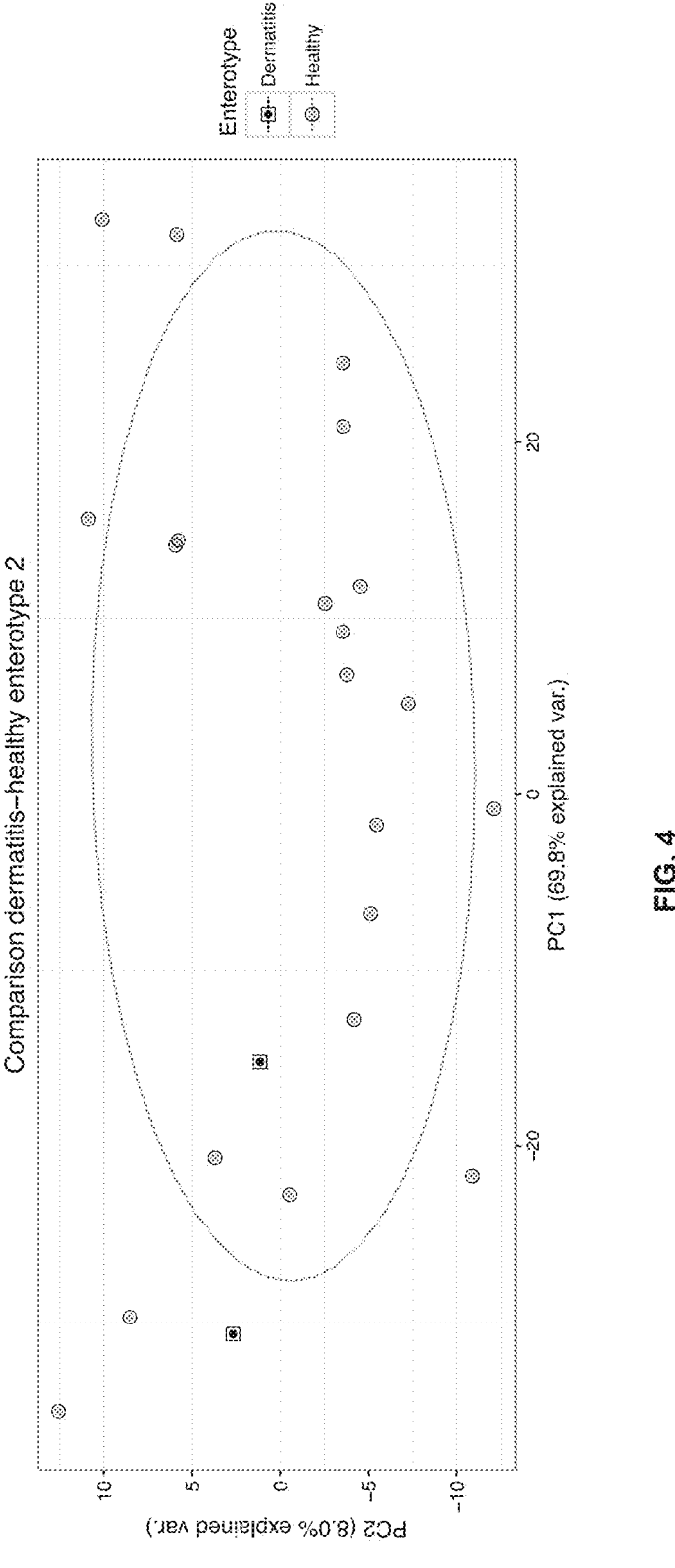
FIG. 4 is a diagram showing the principal components analysis of patients with dermatitis or classified as belonging enterotype 2 (square symbol and black) compared to samples from the healthy population of enterotype 2 (circular symbol and gray). The genres most represented in the samples located in the upper right-hand part of the figure are shown in black while those under-represented in this situation are shown in gray. With respect to the samples located in the lower left-hand corner, the trend is the opposite: the less abundant are marked in black and the abundant are those marked in gray.

FIG. 4 shows the bacterial variability among healthy subjects versus patients with AD, all with enterotype 2. In this case, it is not possible to differentiate, in terms of bacterial genera, among AD patients with enterotype 2 from healthy individuals with the same enterotype. On the other hand, this figure shows the low level of AD patients who are classified as enterotype 2.

Figure 5:
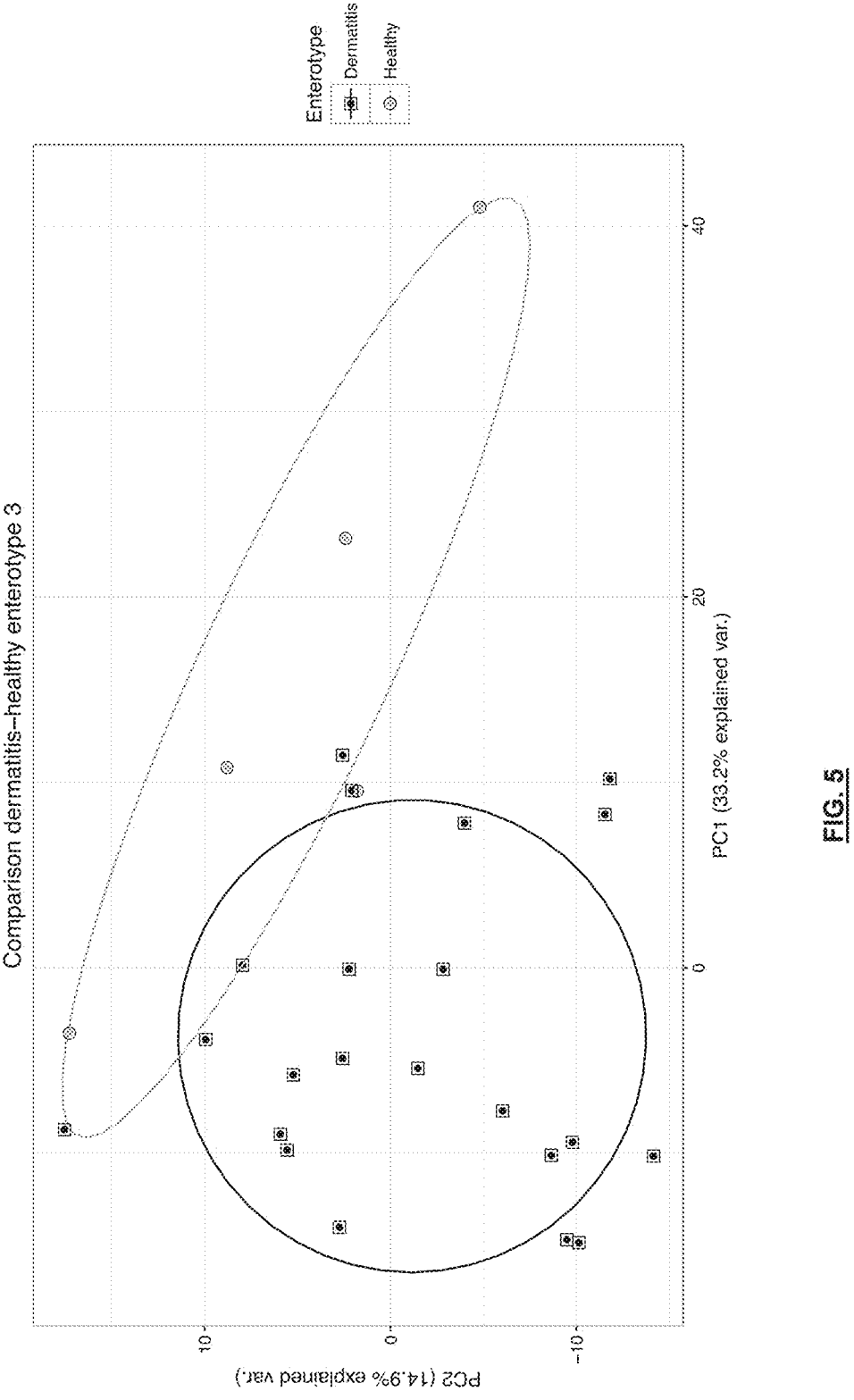
FIG. 5 is a diagram showing the principal components analysis of patients with dermatitis or classified as belonging enterotype 3 (square symbol and black) compared to samples from the healthy population of enterotype 3 (circular symbol and gray). The genres most represented in the samples located in the upper right-hand part of the figure are shown in black and those under-represented in this situation are shown in gray. With respect to the samples located in the lower left-hand corner, the trend is the opposite: the less abundant are marked in black and the abundant are marked in gray.

As is the case for healthy individuals and AD patients with enterotype 1, in AD patients classified as enterotype 3 (FIG. 5) there are appreciable differences between patients with AD compared to healthy individuals. As shown in FIG. 5, AD patients have fewer species belonging to the Ruminococcus genus than healthy patients, as well as less abundance of species belonging to the genus *Faecalibacterium*.

Given all the results shown above, it is clear that the microbiota of patients with AD is different in composition and variability compared to the microbiota of the healthy population. It has also been shown that there are fewer patients with AD belonging to enterotype 2, and furthermore that patients with AD also display increased microbial variability, but with fewer bacteria belonging to species of the important genera in each enterotype, specifically the genera *Bacteroides* and Ruminococcus for enterotypes 1 and 3, respectively.

Example 2: Analysis of the Efficacy of the Probiotic Composition of the Invention in the Prevention and/or Treatment of Atopic Dermatitis (AD)

I. Materials and Methods

In order to evaluate the efficacy of the probiotic composition of the present invention in reducing symptoms, together with the use of topical corticosteroids in the treatment of atopic dermatitis, a randomized pilot clinical, double-blind, placebo-controlled trial was conducted in a group 20 patients suffering atopic dermatitis aged between 4-17 years.

To do so, patients enrolled in the trial were diagnosed with atopic dermatitis according to the criteria of Hanifin and Rajka (Hanifin J M, et al Acta Derm Venereol 1980; 92: 44-7), fulfilling all the inclusion criteria and none of exclusion criteria established in the trial. Trial subjects also used, or might use, topical corticosteroids to treat outbreaks of atopic dermatitis, along with other active ingredients used as normal treatment, such as emollients, systemic corticosteroids, antihistamines, etc.

Each patient was assigned to either the treatment or placebo group using stratified 1:1 randomization by blocks taking into account the variables: sex, age, family history of first degree of consanguinity of atopy or atopic dermatitis and onset of atopic dermatitis before four years of age.

The probiotic composition of the invention comprises *Bifidobacterium lactis* CECT 8145, *Bifidobacterium longum* CECT 7347 and *Lactobacillus casei* CECT 9104, formulated in a sugar and maltrotexina tapioca base, containing $5 \times 10^{10}$ cfu/gram.

The form and appearance of the placebo administered was the same as that of the composition of the invention, but contained only tapioca maltodextrin and sugar.

The dosage regimen of the probiotic composition of the invention or placebo was one capsule per day.

For the treatment of outbreaks of atopic dermatitis that might be experienced by patients enrolled in the trial, methylprednisolone aceponate was used as a topical corticosteroid, and duration of such treatment did not exceed two weeks. Deflazacort was prescribed if treatment with systemic corticosteroids was required. Desloratadine was used to treat itching, and a commonly used antibiotic such as fusidic acid was used for cases of infected atopic dermatitis.

The treatment period lasted twelve weeks from the recruitment of patients up until the last check-up. After the trial inclusion check-up (baseline) and assignment of treatment (treatment group or placebo), seven check-ups were programmed, taking place at weeks 4, 8 and 12 from beginning treatment with the composition of the invention or with the placebo. During these check-ups the SCORAD index was evaluated; and at weeks 2, 6 and 10 each patient's Data Collection Logbook (DCL) was updated.

All medications taken by the patient during the trial were recorded in the patient's medical records and in the DCL, specifying the doses, route of administration and duration of treatment (start and end dates), and including medication. Additionally, each check-up was recorded in the DCL as well as the tally of returned capsules. Table 1 shows the demographic and clinical characteristics of patients at baseline in each treatment group. Table 2 shows the timeline of the trial.

TABLE 1

Baseline demographic and clinical characteristics of the patients in each treatment group.

|  | Treatment | Average | SD | SEM |
|---|---|---|---|---|
| Age | Placebo | 8.96 | 3.940 | 0.804 |
|  | Composition | 9.35 | 3.577 | 0.702 |
| Scorad | Placebo | 31.6417 | 5.05129 | 1.03109 |
|  | Composition | 33.3077 | 3.51351 | .68906 |
| IgE_Baseline | Placebo | 292.08 | 636.537 | 129.933 |
|  | Composition | 428.44 | 723.861 | 144.772 |
| Eosin_Baseline | Placebo | 4.73 | 4.274 | 0.872 |
|  | Composition | 4.96 | 5.799 | 1.160 |

TABLE 1-continued

Baseline demographic and clinical characteristics of the patients in each treatment group.

| | Treatment | Average | SD | SEM |
|---|---|---|---|---|
| V2 Total | Placebo | 3.68 | 4.224 | 0.901 |
| Corticoides* | Composition | 3.00 | 3.240 | 0.648 |
| V2 Total | Placebo | 0.32 | 0.780 | 0.166 |
| Antihistamines* | Composition | 1.28 | 2.072 | 0.414 |

*Days of treatment in 2 weeks;
SD: standard deviation;
SEM: standard error of mean.

TABLE 2

Clinical Trial Protocol.

| | Check-ups | | | | | | |
|---|---|---|---|---|---|---|---|
| | 0/1 | 2 | 3 | 4 | 5 | 6 | 7 |
| | | | | Weeks | | | |
| | 0 | 2 | 4 | 6 | 8 | 10 | 12 |
| Inclusion/exclusion criteria | X | | | | | | |
| Signed informed consent | X | | | | | | |
| Medical record | X | | | | | | |
| Physical examination | X | | X | | X | | X |
| Pregnancy test | X | | | | | | X |
| Complementary examinations | X | | | X | | | |
| SCORAD | X | | X | | X | | X |
| Treatment (probiotic composition or placebo) | X | | X | | X | | |
| Data collection logbook | | X | | X | | X | X |
| Delivery of treatment | X | | X | | X | | |
| Return and tally of unconsumed treatment | | | X | | X | | X |
| Assessment of adverse events | | X | X | X | X | X | X |

All statistical analyzes performed to obtain the final results shown below were carried out using SPSS 20.0 software.

Additionally the trial was undertaken in accordance with the Declaration of Helsinki, as amended in successive world assemblies. The medical record and informed consent letter was obtained for all participants (signed by the patient or his/her guardian or legal representative) in accordance with the Declaration of Helsinki and approved by an ethics and institutional research committee.

II. Results

First we analyzed whether the samples included in each study group were homogeneous, i.e., placebo group and the group receiving the probiotic composition of the invention. Table 3 demonstrates that this requirement was met as no differences were found between any of the variables analyzed for each study group.

TABLE 3

Homogeneity of the two samples. Trial statistics[a]

| | Age | SCORAD | V2 Total Corticosteroids* | V2 Total Antihistamines* |
|---|---|---|---|---|
| Mann-Whitney U test | 286.500 | 260.500 | 271.000 | 223.500 |

TABLE 3-continued

Homogeneity of the two samples. Trial statistics[a]

| | Age | SCORAD | V2 Total Corticosteroids* | V2 Total Antihistamines* |
|---|---|---|---|---|
| Wilcoxon W | 586.500 | 560.500 | 596.000 | 476.500 |
| Z | −0.497 | −1.000 | −0.088 | −1.435 |
| Asymptotic Sig. (bilateral) | 0.619 | 0.317 | 0.930 | 0.151 |

[a]Variable grouping: no differences occur in main variables at baseline;
*Days of treatment in 2 weeks.

As mentioned above mean values (mean and median) and ±standard deviation (SD) were calculated for global data at baseline, at one month and at two and three months of treatment. The values presented by the patient at each of these time points were compared with those taken at the beginning of the trial using the Wilcoxon test.

Effectiveness of the Composition of the Invention a Month after Starting Treatment After one month of treatment the SCORAD index was analyzed, comparing values between groups as well as baseline values. Table 4 shows the changes in value of absolute numbers and as a percentage.

TABLE 4

SCORAD index one month after starting treatment with the probiotic composition of the invention or placebo.

| Treatment | | SCORAD 1 month | % change SCORAD 1 month |
|---|---|---|---|
| Placebo | Mean | 25.8500 | 16.0015 |
| | SD | 8.02355 | 23.17611 |
| | Median | 24.8500 | 18.0150 |
| Composition | Mean | 19.6182 | 41.7586 |
| | SD | 7.33580 | 19.27088 |
| | Median | 19.5000 | 40.8150 |
| Mann-Whitney U test | | 124.500 | 79.000 |
| Wilcoxon W | | 377.500 | 289.000 |
| Z | | −2.406 | −3.551 |
| Asymptotic Sig. (bilateral) | | 0.016 | 0.000 |

As shown by the results in Table 4 and FIG. 6, after a month of treatment there were significant differences in the SCORAD index for the placebo group compared to the group treated with the probiotic composition of the invention. FIGS. 7 and 8 show changes in the SCORAD index at check-ups corresponding to two months (FIG. 7) and three months (FIG. 8) for treatment compared to baseline between the group treated with the probiotic composition of the invention and the placebo group.

Figure 9:
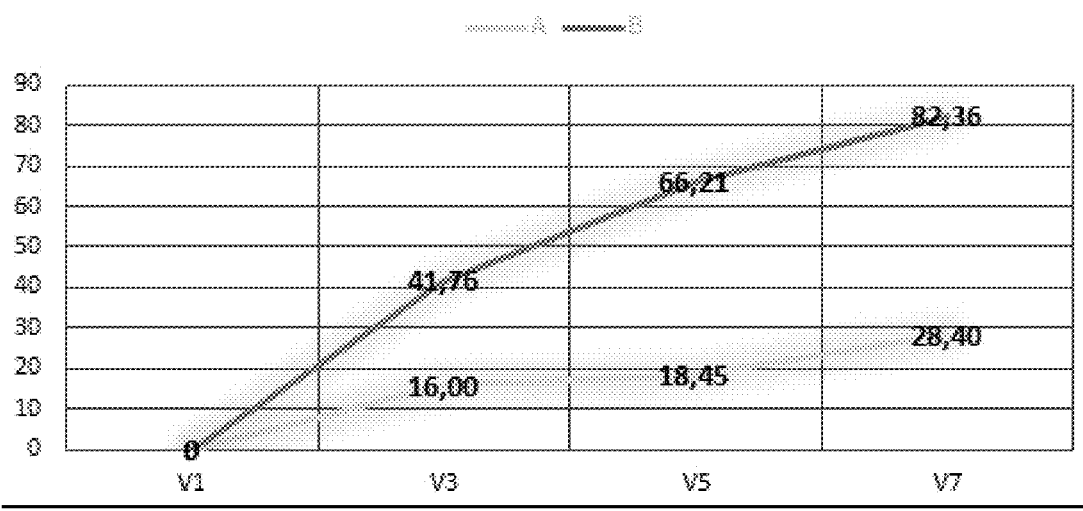
FIG. 9 shows the % of improvement in the SCORAD index during the trial period measured at one month, two months and three months (end of trial) as of baseline. The differences between the two treatment groups were statistically significant as of the first month and these differences increased at months two and three of the trial. The dashed line shows the group consuming the probiotic composition; continuous line, group consuming the placebo.

FIG. 9 shows that the group treated with the composition of the invention has a lower SCORAD index measured at one month, two months and three months from baseline as compared to the placebo group. As seen in FIG. 9, the differences between the two treatment groups are statistically significant already as of the first month of treatment, with these differences increasing at 2 (v5) and 3 (V7) months from baseline.

Figure 10:
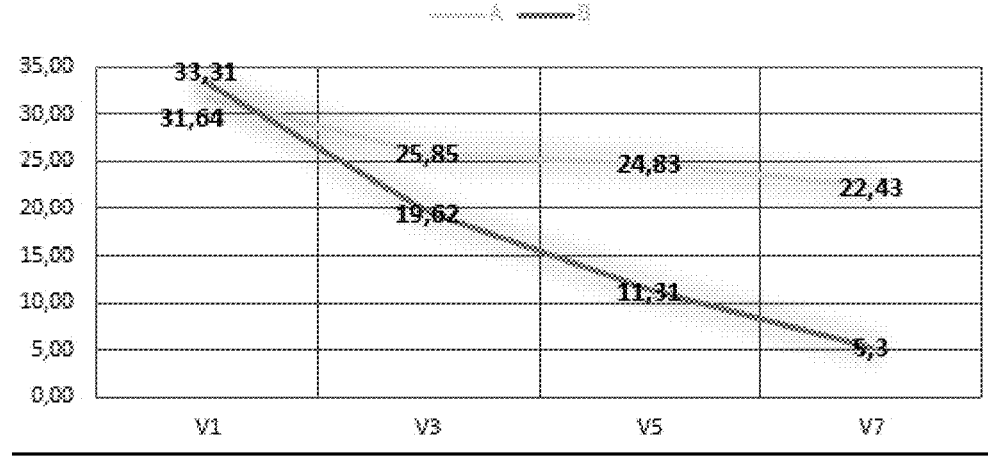
FIG. 10 shows the trends in the SCORAD index over time, measured at one month, two months and three months (end of trial) after baseline. The differences between the two treatment groups are statistically significant. The dashed line represents the group consuming the probiotic composition; the continuous line shows the placebo group.

FIG. 10 shows the trends in the SCORAD index measured at one (V3), two (V5) and three (V7) months after the start of the trial. The differences between the group treated with the composition of the invention and the placebo group were statistically significant, demonstrating the advantages of using the composition in the treatment in patients with AD.

Regarding the use of topical corticosteroids in each study group, at one month of treatment, no statistically significant differences were observed between the two treatment groups for the variable days of use of topical corticosteroids (Table 5) on comparing both treatment groups by the Wilcoxon test with a statistical significance level of five percent (5%). By contrast, a trend was observed when topical corticosteroids were not used, which was greater in the group treated with the probiotic composition of the invention compared to the placebo group, specifically at months 2 and 3 of the trial. Notably, it did not reach statistical significance mainly due to the trial sample size.

TABLE 5

Analysis of topical corticosteroids used in each treatment group one month after the start of the trial. The grouping variable used to obtain the data shown is the kind of treatment, i.e., probiotic composition of the invention or placebo.

| Statistical analysis | V3 Total days of corticoid treatment |
| --- | --- |
| Mann-Whitney U test | 210.500 |
| Wilcoxon W | 441.500 |
| Z | −0.512 |
| Asymptotic Sig. (bilateral) | 0.108 |

No statistically significant differences between the two treatment groups, i.e., probiotic composition of the invention versus placebo, were observed on analyzing the variable for days of antihistamine use in the first month of treatment (Table 6). This variable was analyzed using the Wilcoxon test with a five percent (5%) level of statistical significance for each treatment group.

TABLE 6

Analysis of antihistamines used in each treatment group one month after baseline. The grouping variable used to obtain the data shown is the type of treatment: probiotic composition of the invention versus placebo.

| Statistical analysis | V3 Total days of antihistamine treatment |
| --- | --- |
| Mann-Whitney U test | 220.500 |
| Wilcoxon W | 473.500 |
| Z | −0.578 |
| Asymptotic Sig. (bilateral) | 0.563 |

Table 7 summarizes the data for the efficacy of the probiotic composition of the invention in treating AD after one month of administration, specifically as regards the variables analyzed: SCORAD index, use of topical corticosteroids and antihistamines, as compared to the placebo group.

TABLE 7

SCORAD index, total days of corticosteroid use and total days of antihistamine use in the group treated with the probiotic composition of the invention compared to the placebo group.

| | Treatment | Mean range | Sum of ranges | Statistical significance |
| --- | --- | --- | --- | --- |
| SCORAD 1 month | Placebo | 26.28 | 525.50 | 0.016 |
| | Composition | 17.16 | 377.50 | |
| % improvement | Placebo | 14.45 | 289.00 | 0.000 |
| SCORAD 1 month | Composition | 27.91 | 614.00 | |
| V3 Total | Placebo | 21.02 | 441.50 | 0.608 |
| Corticosteroids | Composition | 22.93 | 504.50 | |

TABLE 7-continued

SCORAD index, total days of corticosteroid use and total days of antihistamine use in the group treated with the probiotic composition of the invention compared to the placebo group.

| | Treatment | Mean range | Sum of ranges | Statistical significance |
| --- | --- | --- | --- | --- |
| V3 Total | Placebo | 22.50 | 472.50 | 0.563 |
| Antihistamines | Composition | 21.52 | 473.50 | |

A multiple linear regression analysis was performed to assess the independent effect of treatment with the probiotic composition of the invention compared to other variables that may influence the SCORAD. In this analysis the SCORAD variable is entered as the dependent variable. In addition to the variable "type of treatment", the following variables were included: "total number of days of antihistamine treatment", "total number of days of corticosteroid treatment" and "SCORAD at baseline" of the clinical trial.

One month after treatment the only variable significantly associated with the SCORAD index is the type of treatment. Accordingly, the group assigned treatment with the probiotic composition of the invention is related to an absolute decrease in the SCORAD of 9.07 points. That is, of the total decrease in SCORAD observed in the group treated with the probiotic composition of the invention during the first month, the composition of the invention is responsible for sixty-six percent (66%) of this change (9.07 out of 13.69 SCORAD points). Neither the variable for total days of antihistamine treatment or total days of corticosteroid treatment is associated with the SCORAD index.

Furthermore, systemic corticosteroid consumption was evaluated in the same way as described for topical corticosteroids consumption, as pre-specified secondary variable. The results obtained for systemic corticosteroid consumption did not show significant differences related to the use of these compounds between the two treatment groups: composition of the invention versus placebo.

Patients enrolled in the trial indicated that they suffered minor adverse effects such as flatulence in the first five days of treatment: thirty percent (30%) of the patients taking the composition of the invention versus fourteen percent (14%) in the placebo group.

In conclusion, in this example the results show that the administration of the probiotic composition of the invention for treating AD provides advantages in terms of efficacy and tolerability as compared to results for patients treated with the placebo. Thus, the parameters analyzed show a significant improvement in the SCORAD index in AD patients treated with the probiotic composition of the invention versus the placebo-treated patient group. This improvement can be observed from the first month of intake of the probiotic composition of the invention, with this improvement being maintained or increased in further analyses at months 2 and 3 of treatment.

Furthermore, regarding the total number of days that patients in each group had to use topical corticosteroids, although the mean is slightly higher in the group taking the probiotic composition of the invention compared to the placebo group (3.3% vs 2.6%), this difference is not significant. Conversely, on analyzing corticoids consumption at the intra-subject or intra-group level (comparing corticosteroid use at baseline and at the end of the study within the same group), a time-course trend of lower steroids consumption is observed in the group taking the probiotic composition of the invention (steroids consumption decreases by fifty-five percent (55%) as compared to the placebo group (eight percent (8%) decrease during the follow-up period), reaching statistical significance in this case.

Example 3: Analysis of the Effects of the Use of the Probiotic Composition of the Invention in Preventing AD Outbreaks Of the twenty (20) AD patients enrolled in the study, an interim analysis was performed of those reaching a SCO-RAD index of 6. This patient group was subjected to specific monitoring until completing the full three-month treatment period. Ten (10) patients received placebo (FIG. 11, black line) and nine (9) patients received probiotic (FIG. 11, gray line).

Figure 11A:
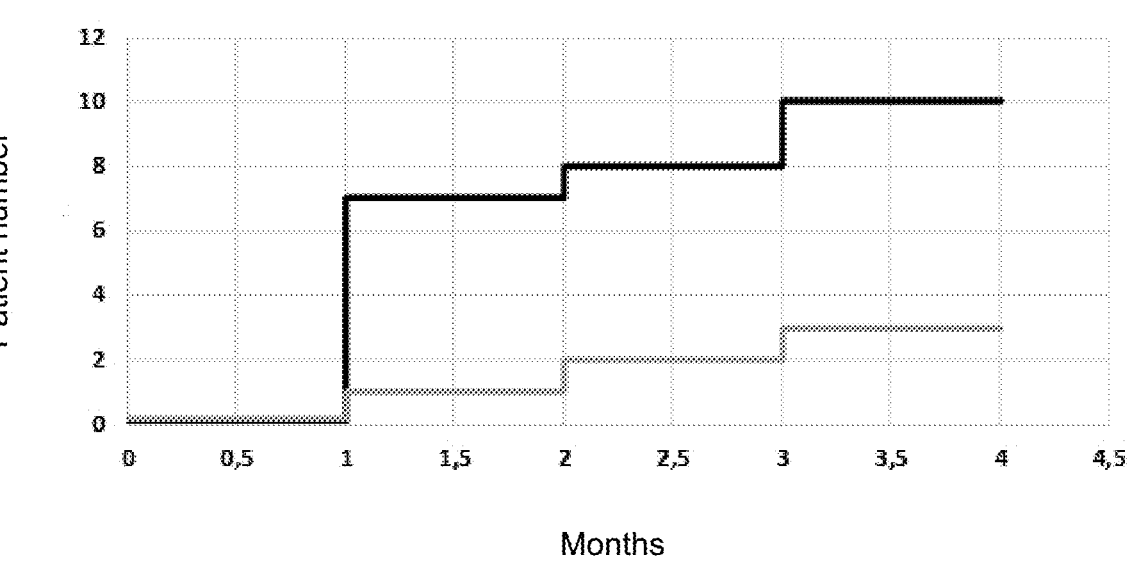
FIG. 11 shows the trend in the number of patients suffering from a new outbreak of atopic dermatitis (FIG. 11A), the total number of patients with new outbreaks of atopic dermatitis (FIG. 11B), and the percentage of patients free from new outbreaks (FIG. 11C); during the three months follow-up after stopping treatment intervention with placebo or probiotic composition of the invention. The differences between the two intervention groups are statistically significant in the three-month evaluation after the start of monitoring for the three variables analyzed. Black line: patients who received placebo; gray line, patients who received the probiotic composition.
Figure 11B:
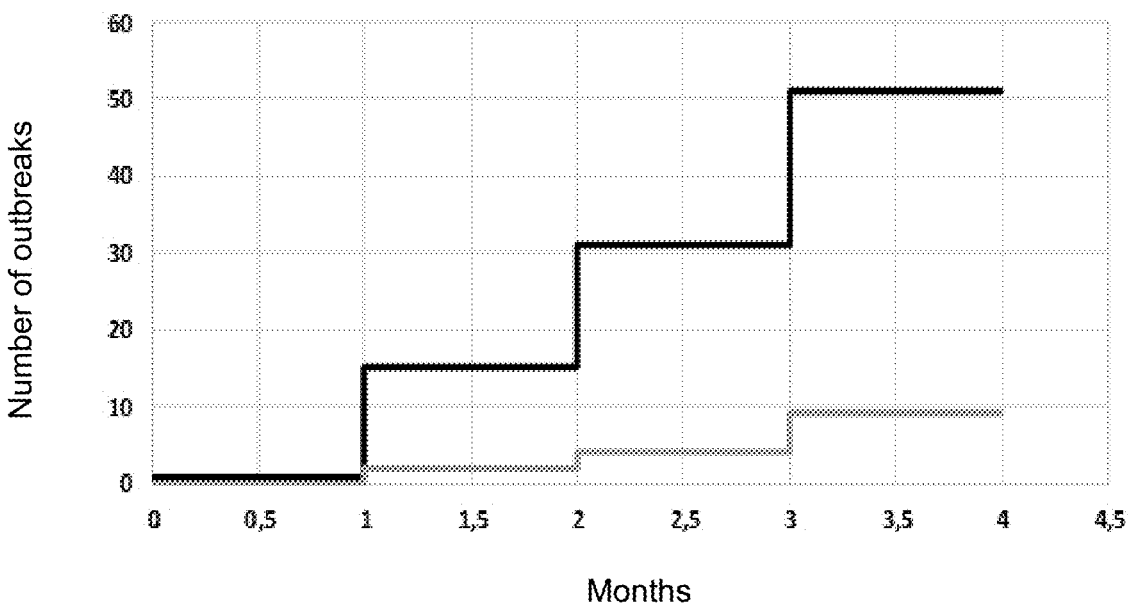
Figure 11C:
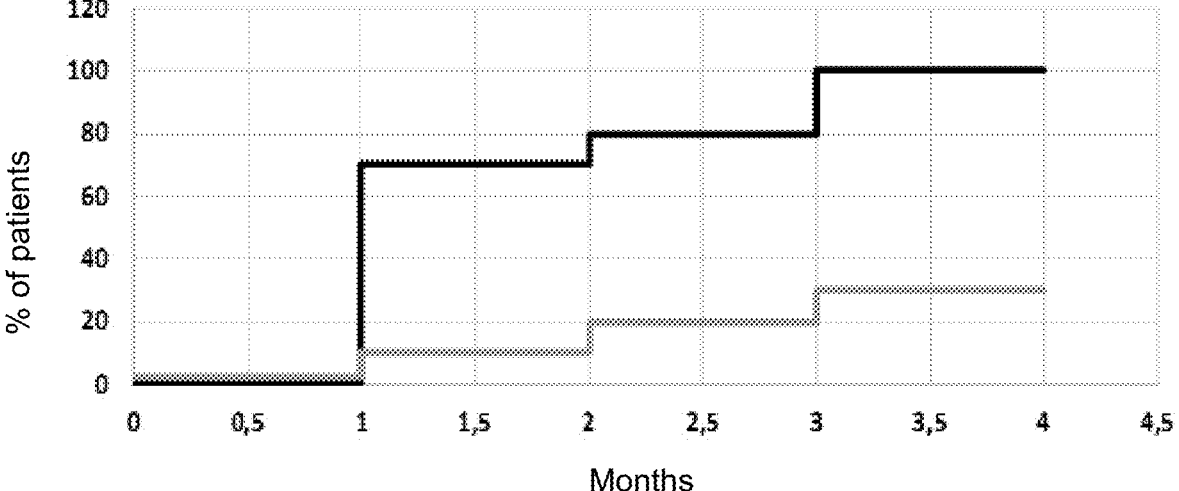

FIG. 11 shows the results for monitoring the number of AD outbreaks in all these patients from the moment of completing the 3-month treatment with the probiotic up until 12 weeks after treatment completion. Thus, FIG. 11 shows the trend in the number of patients suffering from a new AD outbreak (FIG. 11A), the total number of patients with new AD outbreaks (FIG. 11B), and the percentage of patients free from new outbreaks (FIG. 11C); Considering all previously treated patients, FIG. 11 shows that the number of outbreaks, number of patients and percentage of patients suffering new AD outbreaks in the 12-week treatment-free period, is higher among those who had previously received placebo than among those who had previously received the probiotic.

Thus, in this subset of patients, those treated with the probiotic composition of the invention showed a lower relapse and/or deterioration rate than the group treated with the placebo (1 out of 10 (10%) vs 5 out of 9 (55%)), respectively (FIG. 11B).

The differences between the two intervention groups are statistically significant in the three-month evaluation period after monitoring began, for the three variables analyzed.

The data supporting the efficacy of the probiotic in terms of preventing the occurrence of new AD outbreaks are: in the three months after discontinuing treatment with the above-mentioned probiotic composition, individuals who had been treated with said composition had fewer outbreaks and, therefore, a longer time period free of disease than those patients who had not received treatment.

These results demonstrate that the use of the composition of the invention is effective in preventing new outbreaks of AD. Thus, in the three months following discontinuation of treatment with the probiotic composition of the invention, patients who had been treated with said composition had fewer disease outbreaks and therefore a longer disease-free period than patients who had received the placebo.

The invention claimed is:

1. A probiotic composition comprising *Bifidobacterium animalis* subsp. *lactis* (*B. lactis*), *Bifidobacterium longum* and *Lactobacillus casei*, wherein *B. lactis* is *B. lactis* CECT 8145, *B. longum* is *B. longum* CECT 7347 and *L. casei* is *L. casei* CECT 9104, wherein

*B. longum* concentration is 35% with respect to the total concentration of microorganisms present in the composition; *B. lactis* concentration is 35% with respect to the total concentration of microorganisms, and *L. casei* concentration is 30% with respect to the total concentration of microorganisms;

the total concentration of microorganisms of the strains *B. lactis*, *L. casei* and *B. longum* in the composition is from $10^7$ cfu to $10^8$ cfu, and the probiotic composition is a food selected from the group consisting of fruit or vegetable juices and infant formula.

* * * * *